United States Patent [19]

Scartazzini et al.

[11] 4,073,902
[45] Feb. 14, 1978

[54] O-SUBSTITUTED 7β-AMINO-3-CEPHEM-3-OL-4-CARBOXYLIC ACID COMPOUNDS

[75] Inventors: Riccardo Scartazzini, Allschwil; Hans Bickel, Binningen, both of Switzerland

[73] Assignee: Ciba-Geigy Corporation, Ardsley, N.Y.

[21] Appl. No.: 657,908

[22] Filed: Feb. 13, 1976

Related U.S. Application Data

[63] Continuation-in-part of Ser. No. 373,818, June 26, 1973, abandoned.

[30] Foreign Application Priority Data

June 29, 1972 Switzerland .................. 9788/72
Aug. 17, 1972 Switzerland .................. 12195/72
Dec. 22, 1972 Switzerland .................. 18722/72
Feb. 23, 1973 Switzerland .................. 2655/73

[51] Int. Cl.² .............. A61K 31/38; C07D 501/16; C07D 501/60
[52] U.S. Cl. ................................ 424/246; 544/16
[58] Field of Search ............... 260/243 C; 424/246

[56] References Cited

U.S. PATENT DOCUMENTS

| | | | |
|---|---|---|---|
| 3,704,297 | 11/1972 | Dvonch et al. | 260/243 C |
| 3,741,962 | 6/1973 | Breuer | 260/243 C |
| 3,846,417 | 11/1974 | Atwal et al. | 260/243 C |
| 3,907,786 | 9/1975 | Naito et al. | 260/243 C |
| 3,917,588 | 11/1975 | Chauvette | 260/243 C |

*Primary Examiner*—Nicholas S. Rizzo
*Assistant Examiner*—David E. Wheeler
*Attorney, Agent, or Firm*—John J. Maitner

[57] ABSTRACT

The invention relates to O-substituted 7β-amino-3-cephem-3-ol-4-carboxylic acid compounds of the formula

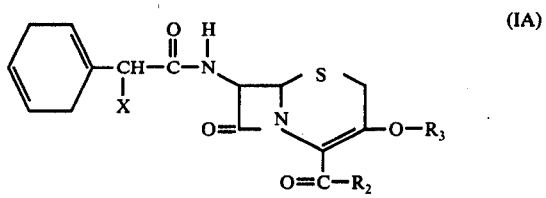

(IA)

wherein X represents amino or substituted amino, $R_2$ represents hydroxyl or a group $R_2^4$ which together with the carbonyl grouping —C(=O)— forms a protected carboxyl group and $R_3$ represents an optionally substituted hydrocarbon radical or an acyl group, and to 1-oxides or 3-cephem compounds of the formula IA, and also to the corresponding 2-cephem compounds of the formula

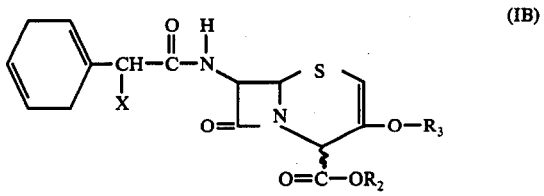

(IB)

wherein X, $R_2$ and $R_3$ have the abovementioned meanings, or salts of such compounds with salt-forming groups. 3-Cephem compounds of the formula IA, particularly those, in which X represents an amino group, $R_2$ is hydroxy and $R_3$ is lower alkyl exhibit pronounced antimicrobial effects, the others, and particularly the 1-oxides of these 3-cephem compounds and the corresponding 2-cephem compounds are useful as intermediates.

18 Claims, No Drawings

O-SUBSTITUTED 7β-AMINO-3-CEPHEM-3-OL-4-CARBOXYLIC ACID COMPOUNDS

CROSS REFERENCE TO RELATED APPLICATION

This is a continuation-in-part of our application Ser. No. 373.818, filed June 26, 1973 now abandoned.

The present invention relates to enol derivatives, especially O-substituted 7β-amino-3-cephem-3-ol-4-carboxylic acid compounds of the formula

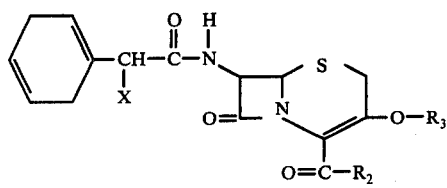

wherein X represents amino or substituted amino, $R_2$ represents hydroxyl or a group $R_2^A$ which together with the carbonyl grouping —C(=O)— forms a protected carboxyl group and $R_3$ represents an optionally substituted hydrocarbon radical or an acyl group, and to 1-oxides of 3-cephem compounds of the formula IA, and also to the corresponding 2-cephem compounds of the formula

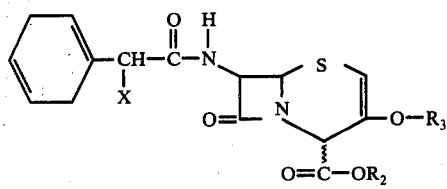

wherein X, $R_2$ and $R_3$ have the abovementioned meanings, or salts of such compounds with salt-forming groups, as well as processes for their manufacture and pharmaceutical preparations containing such compounds having pharmacological effects, and their use.

The enol derivatives of the present invention are ethers and esters of 3-cephem-3-ol or 2-cephem-3-ol compounds.

In 2-cephem compounds of the formula IB having the double bond in the 2,3-position, the optionally protected carboxyl group of the formula —C(=O)—$R_2$ preferably has the α-configuration.

The term "substituted amino" as employed in the above definition of X and throughout the description has reference mainly to "protected amino", however also otherwise substituted amino is comprised, as described further below.

The term "protected amino" has reference to an amino group substituted with one of the commonly employed amino blocking groups, which in a known manner can be replaced by hydrogen without destroying or substantially destroying the β-lactam ring system. Such amino protecting groups and the manner of their preparation and cleavage are well known in the art and described for example in J. F. W. McOmie, "Protective Groups In Organic Chemistry", Plenum Press, New York, N.Y. 1973, Chapter 2, or in E. Schröder and K. Lübke, "The Peptides", Vol. I, Academic Press, 1965, page 72 to 74. Such protected amino groups are for example acylamino, such as lower alkoxycarbonylamino, 2-halogeno-lower alkoxycarbonylamino or optionally substituted phenyl-lower alkoxycarbonylamino such as phenyl-lower alkoxycarbonylamino which contains lower alkoxy, for example methoxy, or nitro, for example tert.-butoxycarbonylamino, 2,2,2-trichloroethoxycarbonylamino, 4-methoxybenzyloxycarbonylamino or diphenylmethyloxycarbonylamino, arylsulphonylamino, for example 4-methylphenylsulphonylamino, tritylamino, arylthioamino, such as nitrophenylthioamino, for example 2-nitrophenylthioamino, or tritylthioamino or 2-propylideneamino which is optionally substituted, such as 2-propylideneamino which contains lower alkoxycarbonyl, for example ethoxycarbonyl, or lower alkanoyl, for example acetyl, such as 1-ethoxycarbonyl-2-propylideneamino.

An otherwise substituted amino group is for example optionally substituted carbamoylamino, such as guanidinocarbonylamino, or sulphoamino which is optionally present in the form of a salt, for example in the form of an alkali metal salt.

The term "protected carboxyl" refers to a group —C(=O)—$R_2^A$, wherein $R_2^A$ can be replaced by the free hydroxy group —OH. Such groups are also well known in the art, for example as cited by J. F. W. McOmie, Chapter 5, and by Schröder and Lübke, page 75.

A protected carboxyl group of the formula —C(=O)—$R_2^A$ is above all an esterified carboxyl group but can also be an anhydride group, usually a mixed anhydride group, or an optionally substituted carbamoyl or hydrazino carbonyl group.

The group $R_2^A$ can therefore be a hydroxyl group etherified by an organic radical, wherein the organic radical preferably contains up to 18 carbon atoms, which together with the —C(=O)— grouping forms an esterified carboxyl group. Examples of such organic radicals are aliphatic, cycloaliphatic, cycloaliphaticaliphatic, aromatic or araliphatic radicals, especially optionally substituted hydrocarbon radicals of this nature, as well as heterocyclic or heterocyclic-aliphatic radicals.

The group $R_2^A$ can also represent an organic silyloxy radical as well as a hydroxyl group esterified by an organometallic radical, such as an appropriate organic stannyloxy group, especially a silyloxy or stannyloxy group which is substituted by 1 to 3, optionally substituted hydrocarbon radicals, preferably with up to 18 carbon atoms, such as aliphatic hydrocarbon radicals, and optionally by halogen, such as chlorine.

A radical $R_2^A$ which forms, with the —C(=O)— grouping and anhydride group, above all a mixed anhydride group, is in particular an acyloxy radical, wherein acyl represents the corresponding acyl radical of an organic carboxylic acid, preferably with up to 18 carbon atoms, such as of an aliphatic, cycloaliphatic, cycloaliphatic-aliphatic, aromatic or araliphatic carboxylic acid or of a carbonic acid half-derivative, such as of a carbonic acid half-ester.

A radical $R_2^A$ which forms a carbamoyl group with a —C(=C)— grouping is an optionally substituted amino group wherein substituents represent optionally substituted monovalent or bivalent hydrocarbon radicals, preferably with up to 18 carbon atoms, such as optionally substituted monovalent or bivalent aliphatic, cycloaliphatic, cycloaliphatic-aliphatic, aromatic or araliphatic hydrocarbon radicals with up to 18 carbon atoms, also appropriate heterocyclic or heterocyclicaliphatic radicals with up to 18 carbon atoms and/or functional groups, such as optionally functionally modified, but especially free, hydroxyl and also etherified or esterified hydroxyl, wherein the etherifying or esterifying radicals have, for example, the abovementioned meanings and preferably contain up to 18 carbon atoms, as well as acyl radicals, above all of organic carboxylic acids and of carbonic acid half-derivatives, preferably with up to 18 carbon atoms.

In a substituted hydrazinocarbonyl group of the formula $—C(=O)—R_2^4$, one or both nitrogen atoms can be substituted, possible substituents being above all optionally substituted monovalent or bivalent hydrocarbon radicals, preferably with up to 18 carbon atoms, such as optionally substituted, monovalent or bivalent aliphatic, cycloaliphatic, cycloaliphatic-aliphatic, aromatic or araliphatic hydrocarbon radicals with up to 18 carbon atoms and also appropriate heterocyclic or heterocyclic-aliphatic radicals with up to 18 carbon atoms and/or functional groups, such as acyl radicals, above all of organic carboxylic acids or of carbonic acid half-derivatives, preferably with up to 18 carbon atoms.

An optionally substituted hydrocarbon radical $R_3$ is preferably an appropriate cycloaliphatic or cycloaliphatic-aliphatic hydrocarbon radical, but especially an optionally substituted aliphatic hydrocarbon radical, and also an appropriate araliphatic hydrocarbon radical. An acyl group $R_3$ is above all the acyl radical of an organic carboxylic acid, including formic acid, such as of a cycloaliphatic, cycloaliphatic-aliphatic, araliphatic, heterocyclic or heterocyclic-aliphatic carboxylic acid, especially the acyl radical of an aliphatic carboxylic acid and also of an aromatic carboxylic acid as well as of a carbonic acid half-derivative.

The general concepts used in the preceding and following description have, for example, the following meanings:

An aliphatic radical, including the aliphatic radical of an appropriate organic carboxylic acid, as well as an appropriate ylidene radical, is an optionally substituted monovalent or divalent aliphatic hydrocarbon radical, especially lower alkyl, as well as lower alkenyl or lower alkinyl, and also lower alkylidene which can contain, for example, up to 7, preferably up to 4, carbon atoms. Such radicals can optionally be monosubstituted, disubstituted or polysubstituted by functional groups, for example by free, etherified or esterified hydroxyl or mercapto groups, such as lower alkoxy, lower alkenyloxy, lower alkylenedioxy, optionally substituted phenyloxy or phenyl-lower alkoxy, lower alkylthio or optionally substituted phenylthio, phenyl-lower alkylthio, heterocyclylthio or heterocyclyl-lower alkylthio, optionally substituted lower alkoxycarbonyloxy or lower alkanoyloxy, or halogen, also by oxo, nitro, optionally substituted amino, for example lower alkylamino, di-lower alkylamino, lower alkyleneamino, oxa-lower alkyleneamino or aza-lower alkyleneamino, as well as acylamino, such as lower alkanoylamino, lower alkoxycarbonylamino, halogeno-lower alkoxycarbonylamino, optionally substituted phenyl-lower alkoxycarbonyamino, optionally substituted carbamoylamino, ureidocarbonylamino or guanidinocarbonylamino and also sulphoamino which is optionally present in the form of a salt, such as in the form of an alkali metal salt, azido, acyl, such as lower alkanoyl or benzoyl, optionally functionally modified carboxyl, such as carboxyl present in the form of a salt, esterified carboxyl, such as lower alkoxycarbonyl, optionally substituted carbamoyl, such as N-lower alkylcarbamoyl or N,N-di-lower alkylcarbamoyl and also optionally substituted ureidocarbonyl or guanidinocarbonyl, or nitrile, optionally functionally modified sulpho, such as sulphamoyl or sulpho present in the form of a salt, or optionally O-monosubstituted or O,O-disubstituted phosphono, wherein substituents represent, for example, optionally substituted lower alkyl, phenyl or phenyl-lower alkyl, it also being possible for O-unsubstituted or O-monosubstituted phosphono to be in the form of a salt, such as in the form of an alkali metal salt.

A bivalent aliphatic radical, including the appropriate radical of a bivalent aliphatic carboxylic acid, is, for example, lower alkylene or lower alkenylene, which can optionally be monosubstituted, disubstituted or polysubstituted, for example like an aliphatic radical indicated above, and/or to be interrupted by heteroatoms, such as oxygen, nitrogen or sulphur.

A cycloaliphatic or cycloaliphatic-aliphatic radical, including the cycloaliphatic or cycloaliphatic-aliphatic radical in an appropriate organic carboxylic acid or an appropriate cycloaliphatic or cycloaliphatic-aliphatic ylidene radical, is an optionally substituted, monovalent or bivalent, cycloaliphatic or cycloaliphatic-aliphatic hydrocarbon radical, for example monocyclic, bicyclic or polycyclic cycloalkyl or cycloalkenyl, and also cycloalkylidene, or cycloalkyl- or cycloalkenyl-lower alkyl or -lower alkenyl, as well as cycloalkyl-lower alkylidene or cycloalkenyl-lower alkylidene, wherein cycloalkyl and cycloalkylidene contains, for example, up to 12, such as 3–8, preferably 3–6, ring carbon atoms, whilst cycloalkenyl contains, for example, up to 12, such as 3–8, for example 5–8, preferably 5 or 6, ring carbon atoms and 1 to 2 double bonds, and the aliphatic part of a cycloaliphatic-aliphatic radical can contain, for example, up to 7, preferably up to 4, carbon atoms. The above cycloaliphatic or cycloaliphatic-aliphatic radicals can, if desired, be monosubstituted, disubstituted or polysubstituted, for example by optionally substituted aliphatic hydrocarbon radicals, such as by the abovementioned optionally substituted lower alkyl groups or, for example, like the abovementioned aliphatic hydrocarbon radicals, by functional groups.

An aromatic radical, including the aromatic radical of an appropriate carboxylic acid, is an optionally substituted aromatic hydrocarbon radical, for example a monocyclic, bicyclic or polycyclic aromatic hydrocarbon radical, especially phenyl, as well as biphenylyl or naphthyl, which can optionally be monosubstituted, disubstituted or polysubstituted, for example like the abovementioned aliphatic and cycloaliphatic hydrocarbon radicals.

A divalent aromatic radical, for example an aromatic carboxylic acid, is above all 1,2-arylene, especially 1,2-phenylene, which can optionally be monosubstituted, disubstituted or polysubstituted, for example like the abovementioned aliphatic and cycloaliphatic hydrocarbon radicals.

An araliphatic radical, including the araliphatic radical in an appropriate carboxylic acid, and also an araliphatic ylidene radical, is, for example, an optionally substituted araliphatic hydrocarbon radical, such as an aliphatic hydrocarbon radical which is optionally substituted and possesses, for example, up to three optionally substituted monocyclic, bicyclic or polycyclic aromatic hydrocarbon radicals, and above all represents phenyl-lower alkyl or phenyl-lower alkenyl as well as phenyl-lower alkinyl and also phenyl-lower alkylidene, it being possible for such radicals to contain, for example, 1–3 phenyl groups and to be optionally monosubstituted, disubstituted or polysubstituted in the aromatic and/or aliphatic part, for example like the abovementioned aliphatic and cycloaliphatic radicals.

Heterocyclic groups, including those in heterocyclicaliphatic radicals, including heterocyclic or heterocyclicaliphatic groups in appropriate carboxylic acids, are especially monocyclic, as well as bicyclic or polycyclic, azacyclic, thiacyclic, oxacyclic, thiazacyclic, thiadiazacyclic, oxazacyclic, diazacyclic, triazacyclic or tetrazacyclic radicals of aromatic character, and also appropriate partially or wholly saturated heterocyclic radicals of this nature and such radicals can optionally be monosubstituted, disubstituted or polysubstituted, for example like the abovementioned cycloaliphatic radicals. The aliphatic part in heterocyclic-aliphatic radicals has, for example, the meaning indicated for the corresponding cycloaliphatic-aliphatic or araliphatic radicals.

The acyl radical of a carbonic acid half-derivative is preferably the acyl radical of an appropriate half-ester, wherein the organic radical of the ester group represents an optionally substituted aliphatic, cycloaliphatic, aromatic or araliphatic hydrocarbon radical or a heterocyclic-aliphatic radical, above all the acyl radical of a lower alkyl half-ester of carbonic acid which is optionally substituted, for example in the $\alpha$- or $\beta$-position, as well as of a lower alkenyl, cycloalkyl, phenyl or phenyl-lower alkyl half-ester of carbonic acid which is optionally substituted in the organic radical. Acyl radicals of a carbonic acid half-ester are furthermore appropriate radicals of lower alkyl half-esters of carbonic acid, in which the lower alkyl part contains a heterocyclic group, for example one of the abovementioned heterocyclic groups of aromatic character, and both the lower alkyl radical and the heterocyclic group can optionally be substituted. The acyl radical of a carbonic acid half-derivative can also be an optionally N-substituted carbamoyl group, such as an optionally halogenated N-lower alkylcarbamoyl group.

An etherified hydroxyl group is above all optionally substituted lower alkoxy, wherein substituents above all represent free or functionally modified, such as etherified or esterified, hydroxyl groups, especially lower alkoxy or halogen, also lower alkenyloxy, cycloalkyloxy or optionally substituted phenyloxy, as well as heterocyclyloxy or heterocyclyl-lower alkoxy especially also optionally substituted phenyl-lower alkoxy.

An optionally substituted amino group is, for example, amino, lower alkylamino, di-lower alkylamino, lower alkyleneamino, oxa-lower alkyleneamino, thia-lower alkyleneamino, aza-lower alkyleneamino, hydroxyamino, lower alkoxyamino, lower alkanoyloxyamino, lower alkoxycarbonylamino or lower alkanoylamino.

An optionally substituted hydrazino group is, for example, hydrazino, 2-lower alkylhydrazino, 2,2-di-lower alkylhydrazino, 2-lower alkoxycarbonylhydrazino or 2-lower alkanoylhydrazino.

Lower alkyl is, for example, methyl, ethyl, n-propyl, isopropyl, n-butyl, isobutyl, sec.-butyl or tert.-butyl, as well as n-pentyl, isopentyl, n-hexyl, isohexyl or n-heptyl, whilst lower alkenyl can, for example, be vinyl, allyl, isopropenyl, 2- or 3-methallyl or 3-butenyl, lower alkinyl can, for example, be propargyl or 2-butinyl and lower alkylidene can, for example, be isopropylidene or isobutylidene.

Lower alkylene is, for example, 1,2-ethylene, 1,2- or 1,3-propylene, 1,4-butylene, 1,5-pentylene or 1,6-hexylene, whilst lower alkenylene is, for example, 1,2-ethenylene or 2-buten-1,4-ylene. Lower alkylene interrupted by hetero-atoms is, for example, oxa-lower alkylene, such as 3-oxa-1,5-pentylene, thia-lower alkylene, such as 3-thia-1,5pentylene, or aza-lower alkylene, such as 3-lower alkyl-3-aza-1,5-pentylene, for example 3-methyl-3-aza-1,5-pentylene.

Cycloalkyl is, for example, cyclopropyl, cyclobutyl, cyclopentyl, cyclohexyl or cycloheptyl as well as adamantyl, whilst cycloalkenyl is, for example, cyclopropenyl, 1-, 2- or 3-cyclopentenyl, 1-, 2- or 3-cyclohexenyl, 3-cycloheptenyl or 1,4-cyclohexadienyl and cycloalkylidene is, for example, cyclopentylidene or cyclohexylidene. Cycloalkyl-lower alkyl or -lower alkenyl is, for example, cyclopropyl-, cyclopentyl-, cyclohexyl- or cycloheptyl-methyl, -1,1- or -1,2-ethyl, -1,1-, -1,2- or 1,3-propyl, -vinyl or -allyl, whilst cycloalkenyl-lower alkyl or -lower alkenyl represents, for example, 1-, 2- or 3-cyclopentenyl-, 1-, 2- or 3-cyclohexenyl- or 1-, 2- or 3-cycloheptenyl-methyl, -1,1- or -1,2-ethyl, -1,1-, -1,2- or -1,3-propyl, -vinyl or -allyl. Cycloalkyl-lower alkylidene is, for example, cyclohexylmethylene, and cycloalkenyl-lower alkylidene is, for example, 3-cyclohexenylmethylene.

Naphthyl is 1- or 2-naphthyl, whilst biphenylyl represents, for example, 4-biphenylyl.

Phenyl-lower alkyl or phenyl-lower alkenyl is, for example, benzyl, 1- or 2-phenylethyl, 1-, 2- or 3-phenylpropyl, diphenylmethyl, trityl, styryl or cinnamyl, naphthyl-lower alkyl is, for example, 1- or 2-naphthylmethyl and phenyl-lower alkylidene is, for example, benzylidene.

Heterocyclic radicals are above all optionally substituted heterocyclic radicals of aromatic character, for example appropriate monocyclic, monoazacyclic, monothiacyclic or monooxacyclic radicals, sush as pyrryl, for example 2-pyrryl or 3-pyrryl, pyridyl, for example 2-, 3- or 4-pyridyl and also pyridinium, thienyl, for example 2- or 3-thienyl, or furyl, for example 2-furyl, bicyclic monoazacyclic, monooxacyclic or monothiacyclic radicals, such as indolyl, for example 2- or 3-indolyl, quinolinyl, for example 2- or 4-quinolinyl, isoquinolinyl, for example 1-isoquinolinyl, benzofuranyl, for example 2- or 3-benzofuranyl, or benzothienyl, for example 2- or 3-benzothienyl, monocyclic diazacyclic, triazacyclic, tetrazacyclic, oxazacyclic, thiazacyclic or thiadiazacyclic radicals, such as imidazolyl, for example 2-imidazolyl, pyrimidinyl, for example 2- or 4-pyrimidinyl, triazolyl, for example 1,2,4-triazol-3-yl, tetrazolyl, for example 1- or 5-tetrazolyl, oxazolyl, for example 2-oxazolyl, isoxazolyl, for example 3- or 4-isoxazolyl, thiazolyl, for example 2-thiazolyl, isothiazolyl, for example 3- or 4-isothiazolyl, or 1,2,4- or 1,3,4-thiadiazolyl, for example, 1,2,4-thiadiazol-3-yl or 1,3,4-thiadiazol-2-yl, or bicyclic diazacyclic, oxazacyclic or thiazacyclic radicals, such as benzimidazolyl, for example 2-benzimidazolyl, benzoxazolyl, for example 2-benzoxazolyl, or benzthiazolyl, for example 2-benzthiazolyl. Appropriate partially or wholly saturated radicals are, for example, tetrahydrothienyl, such as 2-tetrahydrothienyl, tetrahydrofuryl, such as 2-tetrahydrofuryl, or piperidyl, for example 2- or 4-piperidyl. Heterocyclicaliphatic radicals are lower alkyl or lower alkenyl containing heterocyclic groups, especially those mentioned above. The abovementioned heterocyclic radicals can be substituted, for example by optionally substituted aliphatic or aromatic hydrocarbon radicals, especially lower alkyl, such as methyl, or phenyl which is optionally substituted, for example by halogen such as chlorine, for example phenyl or 4-chlorophenyl, or, for example like the aliphatic hydrocarbon radicals, by functional groups.

Lower alkoxy is, for example, methoxy, ethoxy, n-propoxy, isopropoxy, n-butoxy, isobutoxy, sec.-butoxy, tert.-butoxy, n-pentoxy or tert.-pentoxy. These groups can be substituted, for example as in halogen-lower alkoxy, especially 2-halogen-lower alkoxy, for example 2,2,2-trichloroethoxy, 2-chloroethoxy, 2-bromoethoxy or 2-iodoethoxy. Lower alkenyloxy is, for example, vinyloxy or allyloxy, lower alkylenedioxy is, for example, methylenedioxy, ethylenedioxy or isopropylenedioxy, cycloalkoxy is, for example, cyclopentyloxy, cyclohexyloxy or adamantyloxy, phenyl-lower alkoxy is, for example, benzyloxy, 1- or 2-phenylethoxy, diphenylmethoxy or 4,4'-dimethoxydiphenylmethoxy, or heterocyclyloxy or heterocyclyl-lower alkoxy is, for example, pyridyl-lower alkoxy, such as 2-pyridylmethoxy, furyl-lower alkoxy, such as furfuryloxy, or thienyl-lower alkoxy, such as 2-thenyloxy.

Lower alkylthio is, for example, methylthio, ethylthio or n-butylthio, lower alkenylthio is, for example, allylthio, and phenyl-lower alkylthio is, for example, benzylthio, whilst mercapto groups etherified by heterocyclyl radicals or heterocyclyl-aliphatic radicals are especially pyridylthio, for example 4-pyridylthio, imidazolylthio, for example 2-imidazolylthio, thiazolylthio, for example 2-thiazolylthio, 1,2,4- or 1,3,4-thiadiazolylthio, for example 1,2,4-thiadiazol-3-ylthio or 1,3,4-thiadiazol-2-ylthio, or tetrazolylthio, for example 1-methyl-5-tetrazolylthio.

Esterified hydroxyl groups are above all halogen, for example fluorine, chlorine, bromine or iodine, as well as lower alkanoyloxy, for example acetoxy or propionyloxy, lower alkoxycarbonyloxy, for example methoxycarbonyloxy, ethoxycarbonyloxy or tert.-butoxycarbonyloxy, 2-halogeno-lower alkoxycarbonyloxy, for example 2,2,2-trichloroethoxycarbonyloxy, 2-bromoethoxycarbonyloxy or 2-iodoethoxycarbonyloxy, or arylcarbonylmethoxycarbonyloxy, for example phenacyloxycarbonyloxy.

Lower akoxycarbonyl is, for example, methoxycarbonyl, ethoxycarbonyl, n-propoxycarbonyl, isopropoxycarbonyl, tert.-butoxycarbonyl or tert.-pentoxycarbonyl.

N-Lower alkyl- or N,N-di-lower alkyl-carbamoyl is, for example, N-methylcarbamoyl, N-ethylcarbamoyl. N,N-dimethylcarbamoyl or N,N-diethylcarbonyl, whilst N-lower alkylsulphamoyl represents, for example, N-methylsulphamoyl or N,N-dimethylsulphamoyl.

A carboxyl or sulpho present in the form of an alkali metal salt is, for example, a carboxyl or sulpho present in the form of a sodium or potassium salt.

Lower alkylamino or di-lower alkylamino is, for example, methylamino, ethylamino, dimethylamino or diethylamino, lower alkyleneamino is, for example, pyrrolidino or piperidino, oxa-lower alkyleneamino is, for example, morpholino, thia-lower alkyleneamino is, for example, thiomorpholino, and aza-lower alkyleneamino is, for example piperazino or 4-methylpiperazino. Acylamino in particular represents carbamoylamino, lower alkylcarbamoylamino, such as methylcarbamoylamino, ureidocarbonylamino, guanidinocarbonylamino, lower alkoxycarbonylamino, for example methoxycarbonylamino, ethoxycarbonylamino or tert.-butoxycarbonylamino, halogenolower alkoxycarbonylamino, such as 2,2,2-trichloroethoxycarbonylamino, phenyl-lower alkoxycarbonylamino, such as 4-methoxybenzyloxycarbonylamino, lower alkanoylamino, such as acetylamino or propionylamino, and also phthalimido, or sulphoamino optionally present in the form of a salt, such as in the form of an alkali metal salt, for example in the form of a sodium salt or ammonium salt, Lower alkanoyl is, for example, formyl, acetyl, propionyl or pivaloyl.

O-Lower alkyl-phosphono is, for example, O-methyl- or O-ethyl-phosphono, O,O'-di-lower alkyl-phosphono is, for example, O,O'-dimethyl-phosphono or O,O'-diethylphosphono, O-phenyl-lower alkyl-phosphono is, for example, O-benzyl-phosphono, and O-lower alkyl-O'-phenyl-lower alkyl-phosphono is, for example, O-benzyl-O'-methyl-phosphono.

Lower alkenyloxycarbonyl is, for example, vinyloxycarbonyl, whilst cycloalkoxycarbonyl and phenyl-lower alkoxycarbonyl represent, for example, adamantyloxycarbonyl, benzyloxycarbonyl, 4-methoxy-benzyloxycarbonyl, diphenylmethoxycarbonyl or α-4-biphenylyl-α-methyl-ethoxycarbonyl. Lower alkoxycarbonyl, wherein lower alkyl contains, for example, a monocyclic monoazacyclic, monooxacyclic or monothiacyclic group, is, for example, furyl-lower alkoxycarbonyl, such as furfuryloxycarbonyl, or thienyl-lower alkoxycarbonyl, such as 2-thenyloxycarbonyl.

2-Lower alkylhydrazino and 2,2-di-lower alkylhydrazino are, for example, 2-methylhydrazino or 2,2-dimethylhydrazino, 2-lower alkoxycarbonylhydrazino is, for example 2-methoxycarbonylhydrazino, 2-ethoxycarbonylhydrazino or 2-tert.-butoxycarbonylhydrazino and lower alkanoylhydrazino is, for example, 2-acetylhydrazino.

An etherified hydroxyl group $R_2^A$ forms, together with the carbonyl grouping, an esterified carboxyl group which can preferably be split easily or can be converted easily into another functionally modified carboxyl group, such as into a carbamoyl or hydrazinocarbonyl group. Such a group $R_2^A$ is, for example, lower alkoxy, such as methoxy, ethoxy, n-propoxy or isopropoxy, which, together with the carbonyl grouping, forms an esterified carboxyl group, which can easily be converted, especially in 2-cephem compounds, into a free carboxyl group or into another functionally modified carboxyl group.

An etherified hydroxyl group $R_2^A$ which together with a —C(=)— grouping forms an esterified carboxyl group which can be split particularly easily represents, for example, 2-halogeno-lower alkoxy, wherein halogen preferably has an atomic weight above 19. Such a radical forms, together with the —C(=)— grouping, an esterified carboxyl group which can easily be split on treatment with chemical reducing agents under neutral or weakly acid conditions, for example with zinc in the presence of aqueous acetic acid, or an esterified carboxyl group which can easily be converted into such a group and is, for example, 2,2,2-trichloroethoxy or 2-iodoethoxy, also 2-chloroethoxy or 2-bromoethoxy, which can easily be converted into the latter.

An etherified hydroxyl group $R_2^A$ which together with the —C(=)— grouping represents an esterified carboxyl group which can also be split easily on treatment with chemical reducing agents under neutral or weakly acid conditions, for example on treatment with zinc in the presence of aqueous acetic acid, and also on treatment with a suitable nucleophilic reagent, for example sodium thiophenolate, is an arylcarbonylmethoxy group, wherein aryl in particular represents an optionally substituted phenyl group, and preferably phenacyloxy.

The group $R_2^A$ can also represent an arylmethoxy group wherein aryl in particular denotes a monocyclic, preferably substituted, aromatic hydrocarbon radical. Such a radical forms, together with the —C(=)— grouping, an esterified carboxyl group which can easily be split on irradiation, preferably with ultraviolet light, under neutral or acid conditions. An aryl radical in such an arylmethoxy group is in particular lower alkoxyphenyl, for example methoxyphenyl (wherein methoxy above all is in the 3-, 4- and/or 5-position) and/or above all nitrophenyl (wherein nitro is preferably in the 2-position). Such radicals are, in particular, lower alkoxy-benzyloxy, for example methoxy-benzyloxy, and/or nitrobenzyloxy, above all 3- or 4-methoxy-benzyloxy, 3,5-dimethoxybenzyloxy, 2-nitro-benzyloxy or 4,5-dimethoxy-2-nitro-benzyloxy.

An etherified hydroxyl group $R_2^A$ can also represent a radical which, together with the —C(=)— grouping, forms an esterified carboxyl group which can easily be split under acid conditions, for example on treatment with trifluoroacetic acid or formic acid. Such a radical is above all a methoxy group in which methyl is polysubstituted by optionally substituted hydrocarbon radicals, especially aliphatic or aromatic hydrocarbon radicals, such as lower alkyl, for example methyl, and/or phenyl, or is monosubstituted by a carbocyclic aryl group possessing electron-donating substituents or by a heterocyclic group of aromatic character possessing oxygen or sulphur as a ring member, or in which methyl denotes a ring member in a polycycloaliphatic hydrocarbon radical or denotes the ring member which represents the α-position to the oxygen or sulphur atom in an oxacycloaliphatic or thiacycloaliphatic radical.

Preferred polysubstituted methoxy groups of this nature are tert.-lower alkoxy, for example tert.-butoxy or tert.-pentoxy, optionally substituted diphenylmethoxy, for example diphenylmethoxy or 4,4'-dimethoxydiphenylmethoxy, and also 2-(4-biphenylyl)-2-propoxy, whilst a methoxy group which contains the abovementioned substituted aryl group or the heterocyclic group is, for example, α-lower alkoxy-phenyl-lower alkoxy, such as 4-methoxybenzyloxy or 3,4-dimethoxybenzyloxy, or furfuryloxy, such as 2-furfuryloxy. A polycycloaliphatic hydrocarbon radical in which the methyl of the methoxy group represents a branched, preferably triply branched, ring member, is, for example, adamantyl, such as 1-adamantyl, and an abovementioned oxacycloaliphatic or thiacycloaliphatic radical wherein the methyl of the methoxy group is the ring member which represents the α-position to the oxygen atom or sulphur atom, denotes, for example, 2-oxa- or 2-thialower alkylene or -lower alkenylene with 5–7 ring atoms, such as 2-tetrahydrofuryl, 2-tetrahydropropyranyl (sic) or 2,3-dihydro-2-pyranyl or corresponding sulphur analogues.

The radical $R_2^A$ can also represent an etherified hydroxyl group which, together with the —C(=O)— grouping forms an esterified carboxyl group which can be split hydrolytically, for example under weakly basic or weakly acid conditions. Such a radical is, preferably, an etherified hydroxyl group which forms an activated ester group with the —C(=O)— grouping, such as nitrophenyloxy, for example 4-nitrophenyloxy or 2,4-dinitrophenyloxy, nitrophenyl-lower alkoxy, for example 4-nitro-benzyloxy, hydroxy-lower alkylbenzyloxy, for example 4-hydroxy-3,5-tert.-butyl-benzyloxy, polyhalogenophenyloxy, for example 2,4,6-trichlorophenyloxy or 2,3,4,5,6-pentachlorophenyloxy, and also cyanomethoxy, as well as acylaminomethoxy, for example phthaliminomethoxy or succinyliminomethoxy.

The group $R_2^A$ can also represent an etherified hydroxyl group which, together with the carbonyl grouping of the formula —C(=O)—, forms an esterified carboxyl group which can be split under hydrogenolytic conditions and is, for example, α-phenyl-lower alkoxy, which is optionally substituted, for example by lower alkoxy or nitro, such as benzyloxy, 4-methoxybenzyloxy or 4-nitrobenzyloxy.

The group $R_2^A$ can also be an etherified hydroxyl group which, together with the carbonyl grouping —C(=O)—, forms an esterified carboxyl group which can be split under physiological conditions, above all an acyloxymethoxy group, wherein acyl denotes, for example, the radical of an organic carboxylic acid, above all of an optionally substituted lower alkanecarboxylic acid, or wherein acyloxymethyl forms the residue of a lactone. Hydroxyl groups etherified in this way are lower alkanoyloxymethoxy, for example acetoxymethoxy or pivaloyloxymethoxy, amino-lower alkanoyloxymethoxy, especially α-amino-lower alkanoyloxymethoxy, for example glycyloxymethoxy, L-valyloxymethoxy, L-leucyloxymethoxy and also phthalidyloxy.

A silyloxy or stannyloxy group $R_2^A$ preferably contains, as substituents, optionally substituted aliphatic, cycloaliphatic, aromatic or araliphatic hydrocarbon radicals, such as lower alkyl, halogeno-lower alkyl, cycloalkyl, phenyl or phenyl-lower alkyl groups, or optionally modified functional groups, such as etherified hydroxyl groups, for example lower alkoxy groups, or halogen atoms, for example chlorine atoms, and above all represents tri-lower alkylsilyloxy, for example trimethylsilyloxy, halogeno-lower alkoxy-lower alkylsilyl, for example chloromethoxymethylsilyl, or tri-lower alkylstannyloxy, for example tri-n-butylstannyloxy.

An acyloxy radical $R_2^A$ which, together with a —C(=O)— grouping, forms a mixed anhydride group which can be split, preferably hydrolytically, contains, for example, the acyl radical of one of the abovementioned organic carboxylic acids or carbonic acid half-derivatives and is, for example, lower alkanoyloxy which is optionally substituted, such as by halogen, for example fluorine or chlorine, preferably in the α-position, for example acetoxy, pivaloyloxy or trichloroacetoxy, or lower alkoxycarbonyloxy, for example methoxycarbonyloxy or ethoxycarbonyloxy.

A radical $R_2^A$ which, together with a —C(=O)— grouping, forms an optionally substituted carbamoyl or hydrazinocarbonyl group is, for example, amino, lower alkylamino or di-lower alkylamino, such as methylamino, ethylamino, dimethylamino or diethylamino, lower alkylenamino, for example pyrrolidino or piperidino, oxa-lower alkyleneamino, for example morpholino, hydroxylamino, hydrazino, 2-lower alkylhydrazino or 2,2-di-lower alkylhydrazino, for example 2-methylhydrazino or 2,2-dimethylhydrazino.

An optionally substituted aliphatic hydrocarbon radical $R_3$ is, in particular, lower alkyl with up to 7, preferably with up to 4 carbon atoms, such as methyl, ethyl, n-propyl, isopropyl, n-butyl, isobutyl or sec.-butyl, and also lower alkenyl, for example allyl, tert.-amino-lower alkyl, wherein the tert.-amino group is separated from the oxygen atom by at least two carbon atoms, such as 2- or 3-di-lower alkylamino-lower alkyl, for example 2-dimethylaminoethyl, 2-diethylaminoethyl or 3-dimethylaminopropyl, or etherified hydroxy-lower alkyl, wherein the etherified hydroxyl group, especially lower alkoxy, is separated from the oxygen atom by at least two carbon atoms, such as 2- or 3-lower alkoxy-lower alkyl, for example 2-methoxyethyl or 2-ethoxyethyl. An optionally substituted araliphatic hydrocarbon radical $R_3$ is above all an optionally substituted phenyl-lower alkyl radical, especially a 1-phenyl-lower alkyl radical with 1-3 optionally substituted phenyl radicals, such as benzyl or diphenylmethyl, possible substituents being, for example, esterified or etherified hydroxyl, such as halogen, for example fluorine, chlorine or bromine, or lower alkoxy, such as methoxy.

The acyl radical $R_3$ of an aliphatic carboxylic acid is above all optionally substituted lower alkanoyl, for example acetyl, propionyl or pivaloyl, and such radicals can be substituted, for example by esterified or etherified hydroxyl, such as halogen, for example fluorine or chlorine, or lower alkoxy, for example methoxy or ethoxy. The acyl radical $R_3$ of an aromatic carboxylic acid is, for example, optionally substituted benzoyl, such as benzoyl or benzoyl substituted by esterified or etherified hydroxyl, for example halogen, such as fluorine or chlorine, or lower alkoxy, such as methoxy or ethoxy, or lower alkyl, for example methyl. The acyl radical $R_3$ of a carbonic acid half-derivative is, in particular, lower alkoxycarbonyl, such as methoxycarbonyl or ethoxycarbonyl.

Salts are, in particular, those of compounds of the formulae IA and IB having an acid grouping, such as a carboxyl, sulpho or phosphono group, above all metal salts or ammonium salts, such as alkali metal salts and alkaline earth metal salts, for example sodium, potassium, magnesium or calcium salts, as well as ammonium salts with ammonia or suitable organic amines, possible amines for the salt formation being, above all, aliphatic, cycloaliphatic, cycloaliphatic-aliphatic and araliphatic primary, secondary or tertiary monoamines, diamines or polyamines, as well as heterocylic bases, such as lower alkylamines, for example triethylamine, hydroxy-lower alkylamines, for example 2-hydroxyethylamine, bis-(2-hydroxyethyl)-amine or tri-(2-hydroxyethyl)-amine, basic aliphatic esters of carboxylic acids, for example 4-aminobenzoic acid 2-diethylaminoethyl ester, lower alkyleneamines, for example 1-ethyl-piperidine, cycloalkylamines, for example bicyclohexylamine, or benzylamines, for example N,N'-dibenzylethylenediamine, and also bases of the pyridine type, for example pyridine, collidine or quinoline. Compounds of the formulae IA and IB which possess a basic group can also form acid addition salts, for example with inorganic acids, such as hydrochloric acid, sulphuric acid or phosphoric acid, or with suitable organic carboxylic acids or sulphonic acids, for example trifluoroacetic acid or 4-methylphenylsulphonic acid. Compounds of the formulae IA and IB having an acid group and a basic group can also be in the form of internal salts, that is to say in the form of a zwitter-ion. 1-Oxides of compounds of the formula IA having salt-forming groups can also form salts, as described above.

The new compounds of the present invention possess valuable pharmacological properties or can be used as intermediate products for the manufacture of such compounds. Compounds of the formula IA wherein, for example, X, represents amino, $R_2$ denotes hydroxyl or an etherified hydroxyl group $R_2^A$ which, together with the carbonyl group, forms an esterified carboxyl group which can easily be split under physiological conditions, and $R_3$ has the abovementioned meaning, or salts of such compounds having salt-forming groups, are effective, on parenteral and/or oral administration, against micro-organisms such as Gram-positive bacteria, for example *Staphylococcus aureus, Streptococcus pyogenes* and *Diplococcus pneumoniae* (for example in mice at doses of about 0.001 to about 0.02 g/kg s.c. or p.o.), and Gram-negative bacteria, for example, *Escherichia coli, Salmonella typhimurium, Shigella flexneri, Klebsiella pneumoniae, Enterobacter cloacae, Proteus vulgaris, Proteus rettgeri* and *Proteus mirabilis* (for example in mice in doses of about 0.001 to about 0.15 g/kg s.c. or p.o.), and especially also against penicillin-resistant bacteria, together with a low degree of toxicity. These compounds can therefore be used, for example in the form of antibiotically active preparations, for the treatment of corresponding infections.

Compounds of the formula IB or 1-oxides of compounds of the formula IA, wherein X, $R_2$ and $R_3$ have the meanings indicated in the context of the formula IA, or compounds of the formula IA, wherein X denotes protected amino, $R_2$ represents a radical $R_2^A$ which together with the —C(=O)— grouping forms a protected carboxyl group which can preferably be split easily, a carboxyl group protected in this way being different from a carboxyl group which can be split physiologically, and $R_3$ has the abovementioned meanings, are valuable intermediate products which can be converted in a simple manner, for example as is described below, into the abovementioned pharmacologically active compounds.

The invention in particular relates to the 3-cephem-compounds of the formula IA, wherein X denotes amino, as well as substituted amino, $R_2$ represents hydroxyl, lower alkoxy which is optionally monosubstituted or polysubstituted, preferably in the α-position, for example by optionally substituted aryloxy, such as lower alkoxyphenyloxy, for example 4-methoxyphenyloxy, lower alkanoyloxy, for example acetoxy or pivaloyloxy, α-amino-lower alkanoyloxy, for example glycyloxy, L-valyloxy or L-leucyloxy, arylcarbonyl, for example benzoyl, or optionally substituted aryl, such as phenyl, lower alkoxyphenyl, for example 4-methoxyphenyl, nitrophenyl, for example 4-nitrophenyl, or biphenylyl, for example 4-biphenylyl, or is monosubstituted or polysubstituted in the β-position by halogen, for example chlorine, bromine or iodine, such as lower alkoxy, for example methoxy, ethoxy, n-propoxy, isopropoxy, n-butoxy, tert.-butoxy or tert.-pentoxy, bis-phenyloxy-methoxy which is optionally substituted by lower alkoxy, for example bis-4-methoxyphenyloxy-methoxy, lower alkanoyloxy-methoxy, for example acetoxymethoxy or pivaloyloxymethoxy, α-amino-lower alkanoyloxy-methoxy, for example glycyloxymethoxy, phenacyloxy, optionally substituted phenyl-lower alkoxy, especially 1-phenyl-lower alkoxy, such as phenylmethoxy, with such radicals being able to contain 1-3 phenyl radicals which are optionally substituted, for example by lower alkoxy, such as methoxy, nitro or phenyl, for example benzyloxy, 4-methoxy-benzyloxy, 2-biphenylyl-2-propoxy, 4-nitro-benzyloxy, diphenylmethoxy, 4,4'-dimethoxydiphenylmethoxy or trityloxy, or 2-halogeno-lower alkoxy, for example 2,2,2-trichloroethoxy, 2-chloroethoxy, 2-bromoethoxy or 2-iodoethoxy, and also 2-phthalidyloxy, as well as acyloxy, such as lower alkoxycarbonyloxy, for example methoxycarbonyloxy or ethoxycarbonyloxy, or lower alkanoyloxy, for example acetoxy or pivaloyloxy, tri-lower alkylsilyloxy, for example trimethylsilyloxy, or amino or hydrazino which is optionally substituted, for example, by lower alkyl, such as methyl, or hydroxyl, for example amino, lower alkylamino or di-lower alkylamino, such as methylamino or dimethylamino, hydrazino, 2-lower alkylhydrazino or 2,2-di-lower alkylhydrazino, for example 2-methylhydrazino or 2,2-dimethylhydrazino, or hydroxyamino, and $R_3$ represents lower alkyl, for example methyl, ethyl, n-propyl, isopropyl or n-butyl, lower alkenyl, for example allyl, optionally substituted phenyl-lower alkyl, especially 1-phenyl-lower alkyl with 1 or 2 phenyl radicals which are optionally substituted, for example by lower alkoxy, such as methoxy, for example benzyl or diphenylmethyl, or lower alkanoyl, for example acetyl or propionyl, or lower alkoxycarbonyl, for example methoxycarbonyl, as well as benzoyl which is optionally substituted, for example by lower alkyl, such as methyl, lower alkoxy, for example methoxy, or halogen, for example fluorine or chlorine, as well as the 1-oxides thereof, and also the corresponding 2-cephem compounds of the formula IB, or salts of such compounds with salt-forming groups.

Above all, in a 3-cephem compound of the formula IA, and in a corresponding 2-cephem compound of the formula I, and also in a 1-oxide of a 3-cephem compound of the formula IA, or in a salt of such a compound having salt-forming groups, X represents amino and wherein the amino group can also optionally be substituted and represents, for example, a sulphoamino group optionally present in the form of a salt, or an amino group which contains, as substituents, a hydrolytically removable trityl group or above all an acyl group, such as an optionally substituted carbamoyl group, such as an optionally substituted ureidocarbonyl group, for example ureidocarbonyl or N'-trichloromethylureidocarbonyl, or an optionally substituted guanidinocarbonyl group, for example guanidinocarbonyl, or an acyl radical which can be split off, preferably easily, for example on treatment with an acid agent, such as trifluoroacetic acid, or reductivey, such as on treatment with a chemical reducing agent, such as zinc in the presence of aqueous acetic acid, or with catalytic hydrogen, or hydrolytically, or an acyl radical which can be converted into such a radical, preferably a suitable acyl radical of a carbonic acid half-ester, such as one of the abovementioned, for example optionally halogen-substituted or benzoyl-substituted, lower alkoxycarbonyl radicals, for example tert.-butoxycarbonyl, 2,2,2-trichloroethoxycarbonyl, 2-chloroethoxycarbonyl, 2-bromoethoxycarbonyl, 2-iodoethoxycarbonyl or phenacyloxycarbonyl, optionally lower alkoxy-substituted or nitro-substituted phenyl-lower alkoxycarbonyl, for example 4-methoxybenzyloxycarbonyl or diphenylmethoxycarbonyl, or a suitable acyl radical of a carbonic acid half-amide, such as carbamoyl or N-methylcarbamoyl, or an arylthio or aryl-lower alkylthio radical which can be split off with a nucleophilic reagent, such as hydrocyanic acid, sulphurous acid or thioacetic acid amide, for example 2-nitrophenylthio or tritylthio, an arylsulphonyl radical which can be split off by means of electrolytic reduction, for example 4-methylphenylsulphonyl, or a 1-lower alkoxycarbonyl or 1-lower alkanoyl-2-propylidene radical which can be split off with an acid agent, such as formic acid or aqueous mineral acid, for example hydrochloric acid or phosphoric acid, for example 1-ethoxycarbonyl-2-propylidene, and $R_2$ represents hydroxyl, lower alkoxy, especially α-poly-branched lower alkoxy, for example tert.-butoxy, also methoxy or ethoxy, 2-halogeno-lower alkoxy, for example 2,2,2-trichloroethoxy, 2-iodoethoxy or 2-chloroethoxy or 2-bromoethoxy which can easily be converted into 2-iodoethoxy, phenacyloxy, 1-phenyl-lower alkoxy with 1–3 phenyl radicals which are optionally substituted by lower alkoxy or nitro, for example 4-methoxybenzyloxy, 4-nitro-benzyloxy, diphenylmethoxy, 4,4'-dimethoxy-diphenylmethoxy or trityloxy, lower alkanoyloxymethoxy, for example acetoxymethoxy or pivaloyloxymethoxy, α-amino-lower alkanoyloxymethoxy, for example glycyloxymethoxy, 2-phthalidyloxymethoxy, lower alkoxycarbonyloxy, for example ethoxycarbonyloxy, or lower alkanoyloxy, for example acetoxy, and also tri-lower alkylsilyloxy, for example trimethylsilyloxy, and $R_3$ above all represents lower alkyl, for example methyl, ethyl or n-butyl, also lower alkenyl, for example allyl, and 1-phenyl-lower alkyl, for example benzyl or diphenylmethyl, but also lower alkanoyl, for example acetyl or propionyl, lower alkoxycarbonyl, for example methoxycarbonyl, or benzoyl.

The invention above all relates to 3-cephem compounds of the formula IA, wherein X denotes amino, as well as protected amino, such as acylamino, for example α-poly-branched lower alkoxycarbonylamino, such as tert.-butoxycarbonylamino, or 2-halogeno-lower alkoxycarbonylamino, for example 2,2,2-trichloroethoxycarbonylamino, 2-iodoethoxycarbonylamino or 2-bromoethoxycarbonylamino, or optionally lower alkoxysubstituted or nitro-substituted phenyl-lower alkoxycarbonylamino, for example 4-methoxybenzyloxycarbonylamino or diphenylmethoxycarbonylamino, or tritylamino, as well as arylthioamino, for example 2-nitrophenylthioamino, arylsulphonylamino, for example 4-methylphenylsulphonylamino, or 1-lower alkoxycarbonyl-2-propylideneamino, for example 1-ethoxycarbonyl-2-propylideneamino, $R_2$ above all represents hydroxyl and also represents lower alkoxy, especially α-poly-branched lower alkoxy, for example tert.butoxy, 2-halogeno-lower alkoxy, for example 2,2,2-trichloroethoxy, 2-iodoethoxy or 2-bromoethoxy, or diphenylmethoxy which is optionally substituted, for example, by lower alkoxy, for example methoxy, for example diphenylmethoxy or 4,4'-dimethoxydiphenylmethoxy, as well as tri-lower alkylsilyloxy, for example trimethylsilyloxy, and $R_3$ denotes lower alkyl, for example methyl, ethyl or n-butyl, as well as lower alkenyl, for example allyl, or phenyl-lower alkyl, for example benzyl, also lower alkanoyl, for example acetyl or propionyl, or lower alkoxycarbonyl, for example methoxycarbonyl, as well as the 1-oxides of such 3-cephem compounds of the formula IA, and also the corresponding 2-cephem compounds of the formula IB, or salts, especially pharmaceutically usable, non-toxic salts, of such compounds having salt-forming groups, such as alkali metal salts, for example sodium salts, or alkaline earth metal salts, for example calcium salts, or ammonium salts, including those with amines, of compounds wherein $R_2$ represents hydroxy, or internal salts of compounds wherein $R_2$ represents hydroxy and which contain a free amino group X.

Above all, in 3-cephem compounds of the formula IA, and also in corresponding 2-cephem compounds of the formula IB, as well as in salts, especially in pharmaceutically usable nontoxic salts, of such compounds which have salt-forming groups, as in the salts mentioned in the preceding paragraph, X represents amino, as well as protected amino, such as acylamino, for example α-poly-branched lower alkoxycarbonylamino, such as tert.-butoxycarbonylamino, or 2-halogeno-lower alkoxycarbonylamino, for example 2,2,2-trichloroethoxycarbonylamino, 2-iodoethoxycarbonylamino or 2-bromoethoxycarbonylamino, or optionally lower alkoxy-substituted or nitro-substituted phenyl-lower alkoxycarbonylamino, for example 4-methoxybenzyloxycarbonylamino, $R_2$ above all denotes hydroxyl and also lower alkoxy which is optionally halogen-substituted, for example chlorine-substituted, bromine-substituted or iodine-substituted, in the 2-position, especially α-poly-branched lower alkoxy, for example tert.-butoxy, or 2-halogeno-lower alkoxy, for example 2,2,2-trichloroethoxy, 2-iodoethoxy or 2-bromoethoxy, or optionally lower alkoxy-substituted, such as methoxy-substituted, diphenylmethoxy, for example diphenylmethoxy or 4,4'-dimethoxy-diphenylmethoxy, and also tri-lower alkylsilyloxy, for example trimethylsilyloxy, and $R_3$ denotes lower alkyl, for example methyl, ethyl or n-butyl, as well as lower alkenyl, for example allyl, or phenyl-lower alkyl, for example benzyl.

The invention above all relates to 7β-[D-α-amino-α-(1,4-cyclohexadienyl)-acetylamino]-3-lower alkoxy-3-cephem-4-carboxylic acids, wherein lower alkoxy contains up to 4 carbon atoms and represents, for example, ethoxy or n-butoxy, but above all methoxy, and the internal salts thereof, and above all 3-methoxy-7β-[D-α-(1,4-cyclohexadienyl-glycylamino]-3-cephem-4-carboxylic acid and the internal salt thereof; in the above-mentioned concentrations, especially on oral administration, these compounds display excellent antibiotic properties both against Gram-positive and especially against Gram-negative bacteria, with a low order of toxicity.

Thus, 7β-[D-α-amino-α-(1,4-cyclohexadienyl)-acetylamino]-3-methoxy-3-cephem-4-carboxylic acid (I) has been found to have a surprisingly stronger chemotherapeutic activity as compared to 7β-(D-α-amino-α-phenylacetylamino)-3-methoxy-3-cephem-4-carboxylic acid (II), 7β-[D-α-amino-α-(1,4-cyclohexadienyl)-acetylamino]-3-methyl-3-cephem-4-carboxylic acid (cephradine, III) and 7β-(D-α-amino-α-phenylacetylamino)-3-methyl-3-cephem-4-carboxylic acid (cephalexin, IV) against systemic infections due to various bacterial strains in female MF 2 mice.

The $ED_{50}$-values upon oral administration of the four compounds I to IV are compiled in Table I.

Table I

| infecting organism | oral doses | $ED_{50}$ (mg/kg) | | | |
|---|---|---|---|---|---|
| | | I | II | III | IV |
| Staphylococcus aureus 10B | 1* | 3.3 | 6.0 | 6 | 6.6 |
| S. aureus 2999 i⁺p⁺ | 1 | 25 | 210 | 32 | 85 |
| S. aureus 102 (methicillin res.) | 1 | 17.5 | 100 | 76 | 120 |
| Streptococcus pyogenes 38 | 2** | 1.0 | 7.5 | 8 | 6.0 |
| S. pyogenes Aronson | 2 | 1.0 | 2.5 | 5.5 | 6.3 |
| Diplococcus pneumoniae 111/84 | 2 | 8.5 | 16 | 40 | 30 |
| Escherichia coli 205 | 2 | 9.5 | 22 | 52 | 40 |
| E. Coli 205 R⁺TEM | 2 | 7.3 | | | |
| E. coli 205 R⁺$_{TEM}$ | 2 | 7.3 | 48 | 16 | 40 |
| E. coli 2018 | 2 | 3.0 | 15 | 13 | 13 |
| E. coli 2018 R⁺$_{TEM}$ | 2 | 14 | 38 | 38 | 25 |
| E. coli 2 | 2 | ca. 140 | >1000 | >300 | >1000 |
| E. coli 5 | 2 | 7.8 | 13 | >30 | 28 |
| E. coli 9 | 2 | ca. 30 | 210 | ≧300 | 90 |
| E. coli 16 | 2 | >300 | >300 | >300 | >300 |
| E. coli 9-25.1. | 2 | ≧300 | >300 | >300 | >300 |
| E. coli 1239/19 | 2 | 4 | 12 | ca. 25 | 20 |
| Salmonella typhimurium 273 | 2 | 30 | 60 | 80 | 140 |
| S. typhimurium 277 | 2 | 30 | 65 | 110 | 100 |
| Shigella flexneri 11836 | 2 | 25 | 20 | 11 | 7 |
| Klebsiella pneumoniae 327 | 2 | 40 | 75 | 250 | 105 |
| K. pneumoniae 329 | 2 | 17 | 35 | 120 | 47 |
| Enterobacter cloacae P 99 | 2 | >300 | >300 | >1000 | >300 |
| proteus morganii 2359 | 2 | >300 | >300 | >1000 | >1000 |
| P. vulgaris 1076 | 2 | 20 | 25 | 80 | 45 |
| P. rettgeri 856 | 2 | 6.8 | 14 | ≧30 | 15–30 |
| P. mirabilis 774 | 2 | 16 | 54 | ca. 50 | 80 |
| Serratia marcescens 344 | 2 | >300 | >1000 | >1000 | >300 |
| Pasteurella multocid 341 | 2 | 17 | ca. 20 | 110 | 66 |
| Pseudomonas aeruginosa 799 | 2 | >300 | >300 | >300 | >1000 |

*single dose of antibiotic administered immediately after infection
**two doses; the first administered immediately after infection, the second 3 hours later Also the acute toxicity of the compound I of the present invention is more favourable as the acute toxicity of compounds II and IV as shown in Table II.

Table II

| administration | $LD_{50}$ mg/kg in mice | | |
|---|---|---|---|
| | I | II | IV |
| i.p. | 7090[b] (4800–10460) | 3800 ± 290[a] | 540 ± 70[a] |
| p.o. | >6000 | >6000 | 3250 ± 490[a] |

[a]calcultated according to Miller-Tainter ± standard error (Proc. Soc. exp. Biol. Med. 57, 261, 1944)
[b]calculated according to the Probit-method with 95% confidence limits (Goulden A., Methods of Statistical Analysis, J. Wiley and Sons, 1960, p. 404-408, 3rd printing)

Furthermore, compound I of the present invention has a surprisingly stronger bactericidal activity as compared to cephradin (III) and cephalexin (IV), and the solubility in urin is higher as compared to compound II.

The compounds of the formulae IA and IB are obtained by converting a cepham-3-one compound of the formula

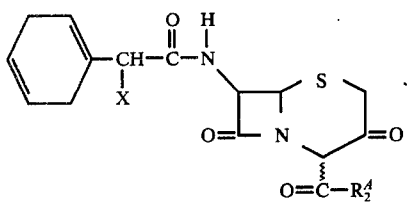

(II)

or a corresponding enol having a double bond in the 2,3- or 3,4-position, or a 1-oxide of such a compound, into an enol derivative having a functionally modified hydroxyl group of the formula —O—R₃ in the 3-position and, if desired, in a resulting compound of the formula IA or IB, converting the protected carboxyl group of the formula —C(=O)—R₂⁴ into the free carboxyl group or into another protected carboxyl group and/or, if desired, within the definition of the products converting a resulting compound into another compound and/or if desired, converting a resulting compound having a salt-forming group into a salt or a resulting salt into the free compound or into another salt and/or, if desired, separating a resulting mixture of isomeric compounds into the individual isomers.

In a starting material of the formula II, $R_2^4$ preferably represents an etherified hydroxyl group $R_2^4$ which, with the —C(=O)— grouping, forms an esterified carboxyl group which can be split, especially under mild conditions, it being possible for functional groups which may be present in a carboxyl protective group $R_2^4$ to be protected in a manner which is in itself known, for example as indicated above. A group $R_2^4$ is, for example, in particular an optionally halogen-substituted lower alkoxy group, such as α-poly-branched lower alkoxy, for example tert.-butoxy, or 2-halogeno-lower alkoxy, wherein halogen represents, for example, chlorine, bromine or iodine, above all 2,2,2-trichloroethoxy, 2-bromoethoxy, or 2-iodoethoxy, or an optionally substituted 1-phenyl-lower alkoxy group, such as a 1-phenyl-lower alkoxy group which contains lower alkoxy, for example methoxy, or nitro, such as benzyloxy or diphenylmethoxy which are optionally substituted, for example as indicated, for example benzyl, 4-methoxybenzyl, 4-nitrobenzyl, diphenylmethoxy or 4,4'-dimethoxy-diphenylmethyl and also an organic silyloxy or stannyloxy group, such as tri-lower alkylsilyloxy, for example trimethylsilyloxy. Preferably, in a starting material of the formula II, the group X denotes protected amino, for example amino protected in a manner which is in itself known, for example, by the abovementioned acyl, trityl, silyl or stannyl groups as well as substituted thio or sulphonyl groups.

Cepham-3-one starting substances of the formula II can be in the keto form and/or in the enol form, with the ring double bond in the 2,3- or 3,4-position. Usually, the starting substances of the formula II are converted from the enol form into the enol derivatives of the formulae IA and IB. Furthermore it is also possible, for example, to employ a mixture of a compound of the formula II and of the corresponding 1-oxide as the starting material and to obtain, as the product, the mixture of compounds of the formulae IA and IB and of the 1-oxide of a compound of the formula IA. It is possible to employ a starting material in the pure form or in the form of the crude reaction mixture obtainable in its manufacture.

The conversion of the starting substances of the formula II into the enol derivatives can be carried out in a manner which is in itself known.

Enol-ethers, that is to say compounds of the formula IA and/or IB, wherein R₃ represents an optionally substituted hydrocarbon radical, are obtained according to any process suitable for the etherification of enol groups. Preferably, the etherifying reagent used is a diazo compound of the formula R₃-N₂ (III) corresponding to the optionally substituted hydrocarbon radical R₃, above all an optionally substituted diazo-lower alkane, for example diazomethane, diazoethane or diazo-n-butane, and also an optionally substituted phenyldiazo-lower alkane such as 1-phenyl-diazolower alkane, for example phenyldiazomethane or diphenyldiazomethane. These reagents are used in the presence of a suitable inert solvent, such as an aliphatic, cycloaliphatic or aromatic hydrocarbon, such as hexane, cyclohexane, benzene or toluene, of a halogenated aliphatic hydrocarbon, for exxample methylene chloride, of a lower alkanol, for example methanol, ethanol or tert.-butanol, or of an ether, such as of a di-lower alkyl-ether, for example diethyl ether, or of a cyclic ether, for example tetrahydrofurane or dioxane, or of a solvent mixture and, depending on the diazo reagent, with cooling, at room temperature or with slight warming and also, if necessary, in a closed vessel and/or under an inert gas atmosphere, for example a nitrogen atmosphere.

Furthermore, enol-ethers of the formula IA and/or IB can be formed by treatment with a reactive ester of an alcohol of the formula R₃—OH (IV) which corresponds to the optionally substituted hydrocarbon radical R₃. Suitable esters are above all those with strong inorganic or organic acids, such as mineral acids, for example hydrogen halide acids, such as hydrochloric acid, hydrobromic acid or hydriodic acid, also sulphuric acid or halogeno-sulphuric acids, for example fluorosulphuric acid, or strong organic sulphonic acids, such as lower alkanesulphonic acids which are optionally substituted, for example by halogen, such as fluorine, or aromatic sulphonic acids, such as, for example, benzenesulphonic acids which are optionally substituted, for example by lower alkyl, such as methyl, halogen, such as bromine, and/or nitro, for example methanesulphonic acid, trifluoromethanesulphonic acid or p-toluenesulphonic acid. These reagents, especially di-lower alkyl sulphates, such as dimethyl sulphate, and also lower alkyl fluorosulphates, for example methyl fluorosulphate, or optionally halogen-substituted methanesulphonic acid lower alkyl esters, for example trifluoromethanesulphonic acid methyl ester, are usually employed in the presence of a solvent, such as of an optionally halogenated, such as chlorinated, aliphatic, cycloaliphatic or aromatic hydrocarbon, for example methylene chloride, of an ether, such as dioxane or tetrahydrofurane, or of a lower alkanol, such as methanol, or of a mixture. At the same time, suitable condensation agents are preferably employed, such as alkali metal carbonates or bicarbonates, for example sodium or potassium carbonate or bicarbonate, (usually together with a sulphate) or organic bases such as, usually sterically hindered, tri-lower alkylamines, for example N,N-diisopropyl-N-ethyl-amine (preferably together with lower alkyl halogenosulphates or optionally halogen-substituted methanesulphonic acid lower alkyl esters), the reaction being carried out with cooling, at room temperature or with warming, for example at temperatures of about −20° C to about 50° C and, if necessary, in a closed vessel and/or in an inert gas atmosphere, for example a nitrogen atmosphere.

Enol-esters can also be manufactured by treatment with a compound containing two or three etherified hydroxyl groups of the formula $R_3$ — O — (V) on the same carbon atom of aliphatic character, that is to say by treatment with an appropriate acetal or ortho-ester, in the presence of an acid agent. Thus, for example, it is possible to use, as etherifying agents, gem-lower alkoxy-lower alkanes, such as 2,2-dimethoxy-propane, in the presence of a strong organic sulphonic acid, such as p-toluenesulphonic acid, and of a suitable solvent, such as of a lower alkanol, for example methanol, or of a di-lower alkylsulphoxide or lower alkylenesulphoxide, for example dimethylsulphoxide, or orthoformic acid tri-lower alkyl esters, for example orthoformic acid triethyl ester, in the presence of a strong mineral acid, for example sulphuric acid or of a strong organic sulphonic acid, such as p-toluenesulphonic acid, and of a suitable solvent, such as of a lower alkanol, for example ethanol, or of an ether, for example dioxane, and thus to arrive at compounds of the formula IA and/or IB, wherein $R_3$ represents lower alkyl, for example methyl or ethyl.

The enol ethers of the formula IA and/or IB can also be obtained if starting substances of the formula II are treated with tri-$R_3$-oxonium salts of the formula $(R_3)_3 O^+A^-$ (VI) (so-called Meerwein salts), as well as di-$R_3O$-carbenium salts of the formula $(R_3O)_2CH^+A^-$ (VIII) or di-$R_3$-halonium salts of the formula $(R_3)_2Hal^+A^-$ (VIII), wherein $A^-$ denotes the anion of an acid and $Hal^+$ denotes a halonium ion, especially a bromonium ion. The salts concerned are above all tri-lower alkyloxonium salts, as well as di-lower alkoxycarbenium salts or di-lower alkylhalonium salts, especially the appropriate salts with complex acids containing fluorine, such as the appropriate tetrafluoborates, hexafluophosphates, hexafluoantimonates or hexachloroantimonates. Such reagents are, for example, trimethyloxonium or triethyloxonium hexafluoantimonate, hexachloroantimonate, hexafluophosphate or tetrafluoborate, dimethoxycarbenium hexafluophosphate or dimethylbromonium hexafluoantimonate. These etherifying agents are preferably used in an inert solvent, such as an ether or a halogenated hydrocarbon, for example diethyl ether, tetrahydrofurane or methylene chloride, or in a mixture thereof, if necessary in the presence of a base, such as of an organic base, for example of a preferably sterically hindered tri-lower alkylamine, for example N,N-diisopropyl-N-ethyl-amine, and with cooling, at room temperature or with slight warming, for example at about $-20°$ to about 50° C, if necessary in a closed vessel and/or in an inert gas atmosphere, for example a nitrogen atmosphere.

The enol-ethers of the formulae IA and/or IB can also be manufactured by treating starting substances of the formula II with a 3-substituted 1-$R_3$-triazene compound (IX) (that is to say a compound of the formula Subst.—N=N—NH—$R_3$), the substituent of the 3-nitrogen atom denoting an organic radical bonded via a carbon atom, preferably a carbocyclic aryl radical, such as an optionally substituted phenyl radical, for example lower alkylphenyl, such as 4-methyl-phenyl. Such triazene compounds are 3-aryl-1-lower alkyl-triazenes, for example 3-(4-methylphenyl)-1-methyl-triazene, 3-(4-methyl-phenyl)-1-ethyl-triazene, 3-(4-methylphenyl)-1-n-propyl-triazene or 3-(4-methylphenyl)-1-isopropyl-triazene, 3-aryl-1-lower alkenyl-triazenes, for example 3-(4-methylphenyl)-allyl-triazene, or 3-aryl-1-phenyl-lower alkyl-triazenes, for example 3-(4-methylphenyl)-1-benzyltriazene. These reagents are usually employed in the presence of inert solvents, such as optionally halogenated hydrocarbons or ethers, for example benzene, or solvent mixtures, and with cooling, at room temperature or preferably at elevated temperature, for example at about 20° to about 100° C, if necessary in a closed vessel and/or in an inert gas atmosphere, for example a nitrogen atmosphere.

Enol-esters, that is to say compounds of the formula IA and/or IB, wherein $R_3$ represents an acyl group, are obtained according to any process suitable for the esterification of enol groups with X in the starting material of the formula II being protected amino, to avoid simultaneous acylation of a free amino group. Thus, preferably carboxylic acids corresponding to the acyl radical, of the formula $R_3$—OH (X) or reactive acid derivatives thereof are used, especially corresponding anhydrides (by which there are also to be understood the internal anhydrides of carboxylic acids, that is to say ketenes, or of carbamic or thiocarbamic acids, that is to say isocyanates or isothiocyanates, or mixed anhydrides, such as those which can be formed, for example, with hydrogen halide acids, such as hydrofluoric acid or hydrochloric acid, with hydrocyanic acid, with halogenoformic acid lower alkyl esters, such as chloroformic acid ethyl esters or isobutyl esters, or with trichloroacetic acid chloride, that is to say the corresponding halides, for example fluorides or chlorides, also pseudohalides, such as cyanocarbonyl compounds corresponding to the carboxylic acids, as well as lower alkoxycarbonyloxycarbonyl, for example ethoxycarbonyloxycarbonyloxy or isobutoxycarbonyloxycarbonyl compounds), or activated esters, such as esters with vinylogous alcohols (that is to say enols), for example esters of lower alkanecarboxylic acids with vinylogous alkanols, for example acetic acid isopropenyl ester, the reaction being carried out, if necessary, in the presence of suitable condensation agents, when using acids, for example, in the presence of carbodiimides compounds, such as dicyclohexylcarbodiimides, or carbonyl compounds such as diimidazolylcarbonyl and when using reacting acid derivatives, for example, in the presence of basic agents, such as trilower alkylamines, for example triethylamine, or heterocyclic bases, for example pyridine, and when using esters with vinylogous alcohols in the presence of an acid agent, such as a mineral acid, for example sulphuric acid, or a strong sulphonic acid, for example p-toluenesulphonic acid. The acylation reaction can be carried out in the absence or in the presence of a solvent or solvent mixture, with cooling, at room temperature or with warming and, if necessary, in a closed vessel and/or in an inert gas atmosphere, for example a nitrogen atmosphere. Suitable solvents are, for example, optionally substituted, especially chlorinated, aliphatic, cycloaliphatic, or aromatic hydrocarbons such as benzene or toluene, it also being possible to use suitable esterification reagents, such as acetic anhydride, as diluents.

In the above etherification or esterification reaction, it is possible to obtain single compounds of the formulae IA or IB or mixtures thereof, depending on the starting material and reaction conditions. Thus, mixtures are obtained, for example, on using starting material of the formula II which is contaminated, for example by heavy metal compounds, such as chromium-II compounds, or, if the starting material of the formula II is not isolated during its manufacture from compounds of the formula XII, on using correspondingly contaminated compounds of the formula XII or on carrying out the reaction under basic conditions; an increasing proportion of compounds of the formula IB is obtained. Mixtures obtained can be separated in a manner which is in itself known, for example with the aid of suitable methods of separation, for example by adsorption and fractional elution, including chromatography (column chromatography, paper chromatography or plate chromatography) using suitable adsorbents, such as silica gel or aluminium oxide, and eluting agents, and also by fractional crystallisation, solvent partitioning and the like.

In the process according to the invention, and in additional measures which may require to be carried out it is possible, if necessary, transiently to protect free functional groups, which do not participate in the reaction, in the starting substances, or in the compounds obtainable according to the process, for example free amino groups by, for example, acylation, tritylation or silylation, free hydroxyl or mercapto groups by, for example, etherification or esterification, and free carboxyl groups by, for example, esterification, including silylation and in each case to liberate them after the reaction has taken place, if desired, individually or conjointly, in a manner which is in itself known. Thus it is preferably possible, for example, to protect the amino group X for example in the form of acylamino groups, such as those mentioned above, for example 2,2,2-trichloroethoxycarbonylamino, 2-bromoethoxycarbonylamino, 4-methoxybenzyloxycarbonylamino, diphenylmethoxycarbonylamino or tert.-butoxycarbonylamino groups, of arylthioamino or aryl-lower alkylthioamino groups, for example 2-nitrophenylthioamino groups, or arylsulphonylamino groups, for example 4-methylphenylsulphonylamino groups, or of 1-lower alkoxycarbonyl-2-propylideneamino groups, and subsequently, optionally after conversion of the protective group, for example of a 2-bromoethoxycarbonyl group into a 2-iodoethoxycarbonyl group, to split the protected group in a manner which is in itself known and depending on the nature of the protective group, for example a 2,2,2-trichloroethoxycarbonylamino or 2-iodoethoxycarbonylamino group by treatment with suitable reducing agents, such as zinc in the presence of aqueous acetic acid, a diphenylmethoxycarbonylamino or tert.-butoxycarbonylamino group by treatment with formic acid or trifluoroacetic acid, an arylthioamino or aryl-lower alkylthioamino group by treatment with a nucleophilic reagent, such as sulphurous acid, an arylsulphonylamino group by means of electrolytic reduction, a 1-lower alkoxycarbonyl-2-propylideneamino group by treatment with an aqueous mineral acid, the splitting being carried out if desired, for example partially.

In a compound of the formula IA or IB obtainable according to the invention and possessing a protected, especially esterified, carboxyl group of the formula $-C(=O)-R_2^4$, the latter can be converted into the free carboxyl group in a manner which is in itself known, for example depending on the nature of the group $R_2^4$. An esterified carboxyl group, for example a carboxyl group esterified by a lower alkyl radical, especially methyl or ethyl, especially in a 2-cephem compound of the formula IB, can be converted into a free carboxyl group by hydrolysis in a weakly basic medium, for example by treatment with an aqueous solution of an alkali metal hydroxide or carbonate or alkaline earth metal hydroxide or carbonate, for example sodium hydroxide or potassium hydroxide, preferably at a pH value of about 9 to 10, and optionally in the presence of a lower alkanol. A carboxyl group esterified by a suitable 2-halogeno-lower alkyl group or by an arylcarbonylmethyl group can be split, for example, by treatment with a chemical reducing agent, such as a metal, for example zinc, or a reducing metal salt, such as a chromium-II salt, for example chromium-II chloride, usually in the presence of a hydrogen donor which is capable of producing nascent hydrogen together with the metal, such as an acid, above all acetic acid and also formic acid, or an alcohol, water being added preferably, a carboxyl group esterified by an arylcarbonylmethyl group can also be split by treatment with a nucleophilic, preferably salt-forming, reagent, such as sodium thiophenolate or sodium iodide, a carboxyl group esterified by a suitable arylmethyl group can be split, for example, by irradiation, preferably with ultraviolet light, for example below 290 m$\mu$, if the arylmethyl group represents, for example, a benzyl radical which is optionally substituted in the 3-, 4- and/or 5-position, for example by lower alkoxy and/or nitro groups, or with ultraviolet light of longer wavelengths, for example above 290 m$\mu$, if the arylmethyl group denotes, for example, a benzyl radical which is substituted by a nitro group in the 2-position, a carboxyl group which is esterified by a suitably substituted methyl group, such as tert.-butyl or diphenylmethyl can be split, for example, by treatment with a suitable acid agent, such as formic acid or trifluoroacetic acid, optionally with the addition of a nucleophilic compound, such as phenol, or anisole, an activated esterified carboxyl group, and also a carboxyl group present in the form of an anhydride, can be split by hydrolysis for example by treatment with an acid or weakly basic aqueous agent, such as hydrochloric acid or aqueous sodium bicarbonate or an aqueous potassium phosphate buffer of pH about 7 to about 9, and an esterified carboxyl group which can be split hydrogenolytically can be split by hydrogenolysis, for example by treatment with hydrogen in the presence of a noble metal catalyst, for example a palladium catalyst.

A carboxyl group protected, for example, by silylation or stannylation can be liberated in the usual manner, for example by treatment with water or an alcohol.

Resulting compounds of the formula IA or IB can be converted in a manner which is in itself known into other compounds of the formula IA or IB.

In a resulting compound it is possible, for example, to split off a protective group from the protected amino group X, especially an easily removable acyl group, in a manner which is in itself known, for example an $\alpha$-poly-branched lower alkoxycarbonyl group, such as tert.-butoxycarbonyl, by treatment with trifluoroacetic acid, and a 2-halogeno-lower alkoxycarbonyl group, such as 2,2,2-trichloroethoxycarbonyl or 2-iodoethoxycarbonyl or a phenacyloxycarbonyl group, by treatment with a suitable reducing metal or corresponding metal compound, for example zinc, or a chromium-II compound, such as chromium-II chloride or chromium-II acetate, advantageously in the presence of an agent which together with the metal or the metal compound generates nascent hydrogen, preferably in the presence of aqueous acetic acid.

The compounds of the formula IA and IB, 1-oxides and salts thereof can also be obtained by acylating a compound of the formula

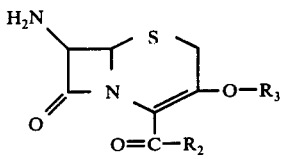

or a 1-oxide or salt thereof, or a compound of the formula

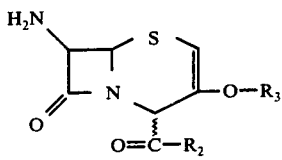

or a salt thereof, wherein $R_2$ and $R_3$ have the meanings given under formula I, according to methods which are in themselves known, for example by treatment with an acid, of the formula

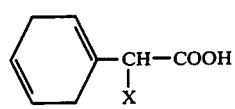

wherein X has the meaning given under formula I, or with a reactive derivative thereof, and, if desired or necessary, in a resulting compound of the formula IA or IB, carrying out additional steps as mentioned under the first process for the preparation of compounds of the formula IA or IB.

If a free acid of the formula IIIa, wherein X is preferably protected amino, is employed for the acylation, suitable condensation agents are usually employed, such as carbodiimides, for example N,N'-diethyl-, N,N'-dipropyl-, N,N'-diisopropyl-, N,N'-dicyclohexyl- or N-ethyl-N'-3-dimethylaminopropyl-carbodiimide, suitable carbonyl compounds, for example carbonyl diimidazole, or isoxazolinium salts, for example N-ethyl-5-phenyl-isoxazolinium-3'-sulphonate and N-tert.-butyl-5-methyl-isoxazolinium perchlorate, or a suitable acylamino compound, for example 2-ethoxy-1-ethoxycarbonyl-1,2-dihydroquinoline.

The condensation reaction is preferably carried out in one of the anhydrous reaction media mentioned later, for example in methylene chloride, dimethylformamide or acetonitrile.

An amide-forming functional derivative of an acid of the formula IIIa, wherein the amino group is preferably protected, including protected by a proton, is above all an anhydride of such an acid, including, and preferably, a mixed anhydride. Mixed anhydrides are, for example those with inorganic acids, especially with hydrogen halide acids, that is to say the corresponding acid halides, for example acid chlorides or acid bromides, and also with hydrazoic acid, that is to say the corresponding acid azides, with an acid containing phosphorus, for example phosphoric acid or phosphorous acid, with an acid containing sulphur, for example sulphuric acid, or with hydrocyanic acid. Further mixed anhydrides are, for example, those with organic acids, such as organic carboxylic acids, such as with lower alkanecarboxylic acids which are optionally substituted, for example by halogen, such as fluorine or chlorine, for example pivalic acid or trichloroacetic acid, or with half-esters, especially lower alkyl half-esters, of carbonic acid, such as the ethyl half-ester or isobutyl half-ester of carbonic acid, or with organic, especially aliphatic or aromatic, sulphonic acids, for example p-toluenesulphonic acid.

It is furthermore possible to use, as acrylating agents internal anhydrides, such as ketenes, for example diketene or isocyanates (that is to say internal anhydrides of carbamic acid compounds).

Further acid derivatives suitable for reaction with the free amino group are activated esters, wherein the optionally present functional groups are usually protected, such as esters with vinylogous alcohols, (that is to say enols), such as vinylogous lower alkanols, or aryl esters, such as phenyl esters which are preferably substituted, for example by nitro or halogen, such as chlorine, for example pentachlorophenyl, 4-nitrophenyl or 2,4-dinitrophenyl esters, hetero-aromatic esters, such as benztriazole esters, or diacylimino esters, such as succinylimino esters or phthalylimino esters.

Further acylation derivatives are, for example, substituted formimino derivatives, such as substituted N,N-dimethylchloroformimino derivatives of acids, or N-substituted N,N-diacylamines, such as a N,N-diacylated aniline.

The acylation with an acid derivative, such as an anhydride, and especially with an acid halide, can be carried out in the presence of an acid-binding agent, for example of an organic base, such as an organic amine, for example a tertiary amine, such as tri-lower alkylamine, for example triethylamine, N,N-di-lower alkylaniline, for example N,N-dimethylaniline, or a base of the pyridine type, for example pyridine, an inorganic base, for example an alkali metal hydroxide, carbonate or bicarbonate or an alkaline earth metal hydroxide, carbonate or bicarbonate, for example sodium hydroxide, carbonate or bicarbonate, potassium hydroxide, carbonate or bicarbonate or calcium hydroxide, carbonate or bicarbonate, or an oxirane, for example a lower 1,2-alkylene oxide, such as ethylene oxide or propylene oxide.

The above acylation can be carried out in an aqueous or, preferably, non-aqueous solvent or solvent mixture, for example in a carboxylic acid amide, such as a N,N-di-lower alkylamide, for example dimethylformamide, a halogenated hydrocarbon, for example methylene chloride, carbon tetrachloride or chlorobenzene, a ketone, for example acetone, an ester, for example ethyl acetate, or a nitrile, for example acetonitrile, or mixtures thereof, and, if necessary, at lowered or elevated temperature and/or in an inert gas atmosphere, for example a nitrogen atmosphere.

In the above N-acylation reactions it is possible to start from compounds of the formula IIa or IIb, wherein $R_2$ has the above meaning, and compounds having free carboxyl groups of the formula $—C(=O)—R_2$, wherein $R_2$ represents hydroxyl, can also be used in the form of salts, for example ammonium salts, such as with triethylamine, or in the form of a compound with a carboxyl group protected by reaction with a suitable organic phosphorus halide compound, such as with a lower alkyl- or lower alkoxy-phosphorus dihalide, such as methyl-phosphorus dichloride, ethyl phosphorus dibromide or methoxyphosphorus dichloride; in the resulting acylation product the protected carboxyl group can be liberated in a manner which is in itself known, for example as described above, including by hydrolysis or alcoholysis.

An acyl group can also be introduced by acylating a compound of the formula IIa or IIb, wherein the 7β-amino group is substituted by an ylidene radical, (which can be introduced, for example by treating a compound wherein the amino group is free, with an aldehyde, such as an aliphatic, aromatic or araliphatic aldehyde), for example according to the methods indicated above, and the acylation product can be hydrolysed, preferably in a neutral or weakly acid medium.

In both reactants, free functional groups can transiently be protected during the acylation reaction, in a manner which is in itself known and be liberated, after the acylation, by means of methods which are in themselves known, for example as described above.

The acylation can also be effected by replacement of an already existing acyl group by another, preferably sterically hindered, acyl group of the formula IIIa, for example by manufacturing the imide-halide compound, treating this with a salt of an acid and splitting off hydrolytically one of the acyl groups present in the product thus obtainable, usually the sterically less hindered acyl group.

In a compound of the formula IA or IB, obtainable according to the process, which contains a free carboxyl group of the formula $-C(=O)R_2$, such a group can be converted into a protected carboxyl group in a manner which is in itself known. Thus, a compound with an esterified carboxyl group is obtained, for example, by treatment with a suitable diazo compound, such as a diazo-lower alkane, for example diazomethane or diazobutane, or a phenyl-diazo-lower alkane, for example diphenyldiazomethane, if necessary in the presence of a Lewis acid, such as, for example, boron trifluoride, or by reaction with an alcohol suitable for the esterification reaction, in the presence of an esterifying agent, such as a carbodiimide, for example dicyclohexylcarbodiimide as well as carbonyldiimidazole, and also with a N,N'-disubstituted O- or S-substituted isourea or isothiourea, wherein a O-substituent and S-substituent are, for example, lower alkyl, especially tert.-butyl, phenyl-lower alkyl or cycloalkyl, and N-substituents or N'-substituents are, for example, lower alkyl, especially isopropyl, cycloalkyl or phenyl, or according to any other known and suitable esterification process, such as reaction of a salt of the acid with a reactive ester of an alcohol and of a strong inorganic acid, or with a strong organic sulphonic acid. Furthermore, acid halides, such as acid chlorides (manufactured, for example, by treatment with oxalyl chloride), activated esters (formed, for example, with N-hydroxy-nitrogen compounds, such as N-hydroxy-succinimide), or mixed anhydrides (obtained, for example, with halogenoformic acid lower alkyl esters, such as chloroformic acid ethyl ester or chloroformic acid isobutyl ester, or with halogenoacetic acid halides, such as trifluoroacetic acid chloride) can be converted into an esterified carboxyl group by reaction with alcohols, optionally in the presence of a base, such as pyridine.

In a resulting compound having an esterified grouping of the formula $-C(=O)-R_2$, this grouping can be converted into a different esterified carboxyl group of this formula, for example 2-chloroethoxycarbonyl or 2-bromoethoxycarbonyl can be converted into 2-iodoethoxycarbonyl by treatment with an iodine salt, such as sodium iodide, in the presence of a suitable solvent, such as acetone.

Mixed anhydrides can be manufactured by reacting a compound of the formula IA or IB, having a free carboxyl group of the formula $-C(=O)-R_2$, preferably a salt, especially an alkali metal salt, for example a sodium salt, or ammonium salt, for example triethylammonium salt, thereof, with a reactive derivative, such as a halide, for example the chloride, of an acid, for example a halogenoformic acid lower alkyl ester or a lower alkanecarboxylic acid chloride.

In a compound obtainable according to the process, having a free carboxyl group of the formula $-C(=O)-R_2$, such a group can also be converted into an optionally substituted carbamoyl or hydrazinocarbonyl group, for which preferably reactive functionally modified derivatives, such as the abovementioned acid halides, and generally esters, including also the abovementioned activated esters, or mixed anhydrides of the appropriate acid are reacted with ammonia or amines, including hydroxylamine, or hydrazines.

A carboxyl group protected by an organic silyl or stannyl group can be formed in a manner which is in itself known, for example by treating compounds of the formulae IA or IB, wherein $R_2$ represents hydroxyl, or salts thereof, such as alkali metal salts thereof, for example sodium salts thereof, with a suitable silylating or stannylating agent, such as one of the abovementioned silylating or stannylating agents; see, for example, British Pat. No. 1,073,530 or Netherlands Published Specification No. 67/17,107.

It is furthermore possible to liberate the protected amino group X, and/or an esterified carboxyl group $R_2^A$, according to methods which are in themselves known, for example those described above, or optionally to modify the free amino group X and/or $R_2$, according to processes which are in themselves known, for example acylation or esterification or substitution. Thus, for example, an amino group can be converted into a sulphoamino group by treatment with sulphur trioxide, preferably in the form of a complex with an organic base, such as a tri-lower alkylamine, for example triethylamine. Furthermore, the reaction mixture obtained by reaction of an acid addition salt of a 4-guanylsemicarbazide with sodium nitrite can be reacted with a compound of the formula IA or IB, wherein X is amino, and the amino group can thus be converted into a free-guanylureido group.

A mixture of a compound of the formula IA and of the corresponding 1-oxide, obtainable according to the process, can be either directly oxidised to the 1-oxide of a compound of the formula IA, or reduced to a 3-cephem compound of the formula IA. These oxidation and reduction steps are described later in connection with the isomerisation of a 2-cephem compound of the formula IB to the corresponding 3-cephem compound of the formula IA, using a 1-oxide as the intermediate product.

Resulting cephem compounds of the formula IA and IB can be converted into 1-oxides of the corresponding 3-cephem compounds of the formula IA by oxidation with suitable oxidising agents, such as those described below. Resulting 1-oxides of 3-cephem compounds of the formula IA can be reduced to the corresponding 3-cephem compounds of the formula IA by reduction with suitable reducing agents such as, for example, those described below. In these reactions it is necessary to ensure that, if necessary, free functional groups are protected and are subsequently again liberated, if desired.

Cephem compounds obtained can be isomerised. Thus, resulting 2-cephem compounds of the formula IB can be converted into the corresponding 3-cephem compounds of the formula IA by isomerising a 2-cephem compound of the formula IB wherein free functional groups can, if appropriate, be protected transiently, for example as indicated. In this reaction it is possible to use, for example, 2-cephem compounds of the formula IB wherein the group of the formula —C(=O)—R$_2$ represents a free or protected carboxyl group, it also being possible to form a protected carboxyl group during the reaction.

Thus it is possible to isomerise a 2-cephem compound of the formula IB by treating it with a weakly basic agent and isolating the corresponding 3-cephem compound of the formula IA from an equilibrium mixture of the 2- and 3-cephem compounds which may be obtained.

Examples of suitable isomerising agents are organic nitrogen-containing bases, such as tertiary heterocyclic bases of aromatic character, and above all tertiary aliphatic, azacycloaliphatic or araliphatic bases, such as N,N,N-tri-lower alkylamines, for example N,N,N-trimethylamine, N,N-dimethyl-N-ethylamine, N,N,N-triethylamine or N,N-diisopropyl-N-ethylamine, N-lower alkyl-azacycloalkanes, for example N-methyl-piperidine, or N-phenyl-lower alkyl-N,N-di-lower alkyl-amines, for example N-benzyl-N,N-dimethylamine, as well as mixtures thereof, such as the mixture of a base of the pyridine type, for example pyridine, and a N,N,N-tri-lower alkylamine, for example pyridine and triethylamine. Furthermore it is also possible to use inorganic or organic salts of bases, especially of medium-strength to strong bases, with weak acids, such as alkali metal salts or ammonium salts of lower alkanecarboxylic acids, for example sodium acetate, triethylammonium acetate or N-methyl-piperidine acetate, as well as other analogous bases or mixtures of such basic agents.

The above isomerisation with basic agents can be carried out for example, in the presence of a derivative of a carboxylic acid which is suitable for forming a mixed anhydride, such as a carboxylic acid anhydride or carboxylic acid halide, for example with pyridine in the presence of acetic anhydride. This reaction is preferably carried out in an anhydrous medium, in the presence or absence of a solvent, such as an optionally halogenated, for example chlorinated, aliphatic, cycloaliphatic or aromatic hydrocarbon, or of a solvent mixture, it being possible for bases used as reactants and liquid under the reaction conditions at the same time also to serve as solvents if necessary with cooling or heating, preferably in a temperature range of about −30° to about +100° C, in an inert gas atmosphere, for example a nitrogen atmosphere, and/or in a closed vessel.

The 3-cephem compounds of the formula IA, thus obtainable, can be separated from 2-cephem compounds of the formula IB which may still be present, in a manner which is in itself known, for example by adsorption and/or crystallisation.

The isomerisation of 2-cephem compounds of the formula IB can also be carried out by oxidising these in the 1-position, if desired separating an isomer mixture of the 1-oxides of 3-cephem compounds of the formula IA which may be obtained and reducing the 1-oxides of the corresponding 3-cephem compounds of the formula IA, thus obtainable. Suitable oxidising agents for the oxidation of 2-cephem compounds in the 1-position are inorganic per-acids which have a reduction potential of at least +1.5 volt and which consist of non-metallic elements, organic per-acids or mixtures of hydrogen peroxide and acids, especially organic carboxylic acids, having a dissociation constant of at least $10^{-5}$. Suitable inorganic per-acids are periodic acid and persulphuric acid. Organic per-acids are appropriate percarboxylic acids and persulphonic acids which can be added as such or can be formed in situ by the use of at least one equivalent of hydrogen peroxide and of a carboxylic acid. It is desirable to use a large excess of the carboxylic acid if, for example, acetic acid is used as the solvent. Suitable per-acids are, for example, performic acid, peracetic acid, pertrifluoroacetic acid, permaleic acid, perbenzoic acid, monoperphthalic acid or p-toluenepersulphuric acid.

The oxidation can also be carried out using hydrogen peroxide and catalytic amounts of an acid having a dissociation constant of at least $10^{-5}$, it being possible to employ low concentrations, for example 1-2% or less, but also larger amounts, of the acid. The activity of the mixture above all depends on the strength of the acid. Examples of suitable mixtures are those of hydrogen peroxide with acetic acid, perchloric acid or trifluoroacetic acid.

The above oxidation can be carried out in the presence of suitable catalysts. Thus, for example, the oxidation with percarboxylic acids can be catalysed by the presence of an acid having a dissociation constant of at least $10^{-5}$, its activity depending on its strength. Acids suitable as catalysts are, for example, acetic acid, perchloric acid and trifluoroacetic acid. Usually, at least equimolar amounts of the oxidising agent, and preferably a small excess of about 10% to about 20%, are used. The oxidation is carried out under mild conditions, for example at temperatures of about −50° to about +100° C, preferably of about −10° to about +40° C.

The oxidation of 2-cephem compounds to the 1-oxides of the corresponding 3-cephem compounds can also be carried out by treatment with ozone, as well as with organic hypohalite compounds, such as lower alkyl hypochlorites, for example tert.butylhypochlorite, which are used in the presence of inert solvents, such as optionally halogenated hydrocarbons, for example methylene chloride, and at temperatures of about −10° to about +30° C, with periodate compounds, such as alkali metal periodates, for example potassium periodate, which are preferably used in an aqueous medium at a pH value of about 6 and at temperatures of about −10° to about +30° C, with iodobenzene dichloride, which is used in an aqueous medium, preferably in the presence of an organic base, for example pyridine, and with cooling, for example at temperatures of about −20° to about 0°, or with any other oxidising agent which is suitable for conversion of a thio group into a sulphoxide grouping.

In the 1-oxides of 3-cephem compounds of the formula IA, thus obtainable, especially in those compounds in which X and R$_2$ have the abovementioned preferred meanings, the groups X and/or R$_2$ can, within the defined framework, be converted into one another, split off or introduced. A mixture of isomeric α- and β-1-oxides can be separated, for example chromatographically.

The reduction of the oxides of 3-cepham compounds of the formula IA can be carried out in a manner which is in itself known, by treatment with a reducing agent, if necessary in the presence of an activating agent. Possible reducing agents are: catalytically activated hydrogen, using noble metal catalysts which contain palladium, platinum or rhodium and which are optionally employed together with a suitable carrier, such as charcoal or barium sulphate; reducing tin, iron, copper or manganese cations, which are used in the form of appropriate compounds or complexes of inorganic or organic nature, for example as tin-II chloride, fluoride, acetate or formate, iron-II chloride, sulphate, oxalate or succinate, copper-I chloride, benzoate or oxide, or manganese-II chloride, sulphate, acetate or oxide, or as complexes, for example with ethylenediaminetetraacetic acid or nitrilotriacetic acid; reducing dithionite, iodide or ferrocyanide anions which are used in the form of appropriate inorganic or organic salts, such as alkali metal salts, for example sodium dithionite or potassium dithionite, sodium iodide or potassium iodide, or sodium ferrocyanide or potassium ferrocyanide, or in the form of the corresponding acids, such as hydriodic acid reducing trivalent inorganic or organic phosphorus compounds, such as phosphines, and also esters, amides and halides of phosphinous, phosphonous or phosphorous acids, as well as phosphorus-sulphur compounds corresponding to these phosphorus-oxygen compounds, in which compounds organic radicals above all represent aliphatic, aromatic or araliphatic radicals, for example optionally substituted lower alkyl, phenyl or phenyl-lower alkyl groups, such as, for example, triphenylphosphine, tri-n-butylphosphine, diphenylphosphinous acid methyl ester, diphenylchlorophosphine, phenyldichlorophosphine, benzenephosphonous acid dimethyl ester, butanephosphonous acid methyl ester, phosphorous acid triphenyl ester, phosphorous acid trimethyl ester, phosphorus trichloride, phosphorus tribromide and the like; reducing halogenosilane compounds which possess at least one hydrogen atom bonded to the silicon atom and which, in addition to halogen, such as chlorine, bromine or iodine, can also possess organic radicals, such as aliphatic or aromatic groups, for example optionally substituted lower alkyl or phenyl groups, such as chlorosilane, bromosilane, dichlorosilane or trichlorosilane, dibromosilane or tribromosilane, diphenylchlorosilane, dimethylchlorosilane and the like; reducing quaternary chloromethylene-iminium salts, especially chlorides or bromides, wherein the iminium group is substituted by a bivalent or two monovalent radicals, such as optionally substituted lower alkylene or lower alkyl groups, such as N-chloromethylene-N,N-diethyliminium chloride or N-chloromethylene-pyrrolidinium chloride; and complex metal hydrides, such as sodium borohydride, in the presence of suitable activating agents, such as cobalt-II chloride, as well as borane dichloride.

As activating agents which are used together with those of the abovementioned reducing agents which do not themselves possess Lewis acid properties, that is to say which above all are employed together with the dithionite, iodide or ferrocyanide reducing agents or the trivalent phosphorus reducing agents which do not contain halogen, or in the catalytic reduction, there should especially be mentioned organic carboxylic acid halides and sulphonic acid halides, also sulphur halides, phosphorus halides or silicon halides having the same or a greater second order hydrolysis constant than benzoyl chloride, for example phosgene, oxalyl chloride, acetic acid chloride or acetic acid bromide, or chloroacetic acid chloride; pivalic acid chloride, 4-methoxybenzoic acid chloride, 4-cyanobenzoic acid chloride, p-toluenesulphonic acid chloride, methanesulphonic acid chloride, thionyl chloride, phosphorus oxychloride, phosphorus trichloride, phosphorus tribromide, phenyldichlorophosphine, benzenephosphonous acid dichloride, dimethyldichlorosilane or trichlorosilane and also suitable acid anhydrides, such as trifluoroacetic acid anhydride, or cyclic sultones, such as ethanesultone, 1,3-propanesultone, 1,4-butanesultone or 1,3-hexanesultone.

The reduction is preferably carried out in the presence of solvents or mixtures thereof, the choice of which is above all determined by the solubility of the starting substances and the choice of the reducing agents, such as, for example, lower alkanecarboxylic acids or esters thereof, such as acetic acid and ethyl acetate, in the case of the catalytic reduction and, for example, optionally substituted, such as halogenated or nitrated, aliphatic, cycloaliphatic, aromatic or araliphatic hydrocarbons, for example benzene, methylene chloride, chloroform or nitromethane, suitable acid derivatives, such as lower alkanecarboxylic acid esters or nitriles, for example ethyl acetate or acetonitrile, or amides of inorganic or organic acids, for example dimethylformamide or hexamethylphosphoramide, ethers, for example diethyl ether, tetrahydrofurane or dioxane, ketones, for example acetone, or sulphones, especially aliphatic sulphones, for example dimethylsulphone or tetramethylenesulphone, and the like, in the case of the chemical reducing agents, these solvents preferably not containing any water. The reaction is usually carried out at temperatures of about $-20°$ to about $100°$ C, it being possible to carry out the reaction at lower temperatures if very reactive activating agents are used.

In the 3-cephem compounds of the formula IA, thus obtainable, X and/or $R_2$ can be converted into other groups X or $R_2$ as described above, it being necessary to bear in mind that the 3-cephem compounds are considerably more sensitive towards basic agents than the corresponding 2-cephem compounds of the formula IB.

Furthermore, 3-cephem compounds can be isomerised to 2-cephem compounds in a manner which is in itself known, and this reaction can be carried out by treatment with a base, preferably an organic base, such as a heterocyclic base, for example pyridine and/or a tertiary amine, such as a tri-lower alkylamine, for example triethylamine, and, if a free 3-cephem-4-carboxylic acid compound is used, additionally in the presence of a suitable acid derivative which can form a mixed anhydride group, such as a carboxylic acid anhydride, such as a lower alkanecarboxylic acid anhydride, for example acetic anhydride. The desired 2-cephem compound can be isolated, in a manner which is in itself known, from an equilibrium mixture of the 2- and 3-cephem compounds which may be obtained.

Salts of compounds of the formulae IA and IB can be manufactured in a manner which is in itself known. Thus, salts of such componds which possess acid groups can be formed, for example, by treatment with metal compounds, such as alkali metal salts, of suitable carboxylic acids, for example the sodium salt of α-ethylcaproic acid, or with ammonia or a suitable organic amine, preferably using stoichiometric amounts or only a small excess of the salt-forming agent. Acid addition salts of compounds of the formulae IA and IB having basic groupings are obtained in the customary manner, for example by treatment with an acid or with a suitable anion exchange reagent. Internal salts of compounds of the formulae IA and IB which contain a salt-forming amino group and a free carboxyl group can be formed, for example, by neutralising salts, such as acid addition salts, to the isoelectric point, for example with weak bases, or by treatment with liquid ion exchangers. Salts of 1-oxides of compounds of the formula IA having salt-forming groups can be manufactured analogously.

Salts can be converted into the free compounds in the customary manner, metal salts and ammonium salts, for example, by treatment with suitable acids, and acid addition salts, for example, by treatment with a suitable basic agent.

Resulting mixtures of isomers can be separated into the individual isomers according to methods which are in themselves known, mixtures of diastereomeric isomers, for example, by fractional crystallisation, adsorption chromatography (column chromatography or thin layer chromatography) or other suitable separation processes. Resulting recemates can be separated into the antipodes in the usual manner, if appropriate after introducing suitable salt-forming groupings, for example by forming a mixture of diastereomeric salts with optically active salt-forming agents, separating the mixture into the diastereomeric salts and converting the separated salts into the free compounds, or by fractional crystallisation from optically active solvents.

The process also encompasses those embodiments according to which compounds arising as intermediate products are used as starting substances and the remaining process steps are carried out with these, or the process is stopped at any stage; furthermore, starting substances can be used in the form of derivatives or be formed during the reaction.

Preferably, those starting substances are used, and the rection conditions are so chosen, that the compounds initially mentioned as being particularly preferred are obtained.

The starting compounds of the formula II used according to the invention can be manufactured, for example, by converting the acetoxymethyl group in a cephem compound of the formula

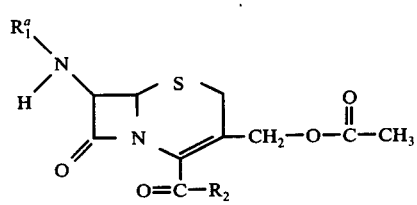

(XI)

wherein $R_1^a$ preferably represents an amino protective group $R_1^4$, for example phenylacetyl, and wherein $R_2$ preferably represents hydroxyl, but also represents a group $R_2^4$, into the hydroxymethyl group, for example by hydrolysis in a weakly basic medium, such as with an aqueous sodium hydroxide solution at pH 9–10, or by treatment with a suitable esterase, such as an appropriate enzyme from Rhizobium tritolii, Rhizobium lupinii, Rhizobium japonicum or Bacillus subtilis, functionally modifying a free carboxyl group of the formula —C(=O)—$R_2$ in a suitable manner, for example esterifying it by treatment with a diazo compound, such as diphenyldiazomethane, and converting the hydroxymethyl group into a halogenomethyl group, for example a chloromethyl or iodomethyl group, for example by treatment with a halogenating agent, such as a chlorinating agent, for example thionyl chloride, or an iodinating agent, such as N-methyl-N,N′-di-cyclohexylcarbodiimidium iodide. A chloromethyl group is converted into the methylene group either directly, for example by treatment with a suitable chromium-II compound, such as an inorganic or organic salt of divalent chromium, for example chromium-II chloride or chromium-II acetate, in a suitable solvent, such as dimethylsulphoxide, or indirectly via the iodomethyl group (which can be formed, for example, by treating the chloromethyl compound with a metal iodide, such as sodium iodide, in a suitable solvent, such as acetone), by treatment of such an iodomethyl compound with a suitable reducing agent, such as zinc in the presence of acetic acid. The methylene group in a compound of the formula

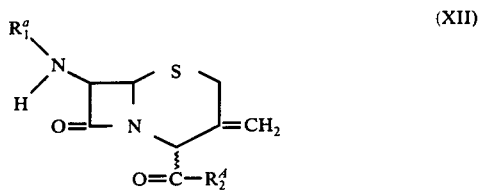

(XII)

wherein $R_1^a$ is hydrogen or an amino protective group $R_1^4$, which is also obtainable from compounds of the formula XI by, for example, electrochemical reduction or reduction with chromium-II salts or aluminium amalgam, is oxidatively degraded according to the process described below. In a cepham-3-one compound thus obtainable, in which $R_1^a$ represents hydrogen, the free amino group can be protected by an appropriate protective group, for example according to the process described above.

In an obtained 3-methylene compound of the formula (XII), wherein the 7β-amino group is still protected by a group $R_1^4$, the protected amino group in the 7-position is liberated in a manner, which is itself known.

An amino protective group $R_1^4$ is a group which can be replaced by hydrogen, above all an acyl group Ac, also a triarylmethyl group, especially the trityl group, as well as an organic silyl group, and an organic stannyl group. A group Ac above all represents the acyl radical of an organic carboxylic acid, preferably with up to 18 carbon atoms, especially the acyl radical of an optionally substituted aliphatic, cycloaliphatic, cycloaliphatic-aliphatic, aromatic, araliphatic, heterocyclic or heterocyclic-aliphatic carboxylic acid (including formic acid) and the acyl radical of a carbonic acid half-derivative.

In a resulting 3-methylene-compound an acyl group $R_1^4$, wherein optionally present free functional groups are optionally protected, amino groups, for example, in the form of acylamino groups or silylated amino groups and/or carboxyl groups, for example, in the form of esterified or silylated carboxyl groups, is split off, for example, by treatment with an imide-halide-forming agent, reaction of the resulting imide-halide with an alcohol and splitting of the iminoether formed.

Imide-halide-forming agents in which halogen is bonded to an electrophilic central atom are above all acid halides, such as acid bromides and especially acid chlorides. The acid halides are above all acid halides of inorganic acids, above all of acids containing phosphorus, such as phosphorus oxyhalides, phosphorus trihalides and especially phosphorus pentahalides, for example phosphorus oxychloride, phosphorus trichloride and above all phosphorus pentachloride, and also pyrocatechyl-phosphorus trichloride, as well as acid halides, especially acid chlorides, of acids containing sulphur or of carboxylic acids, such as thionyl chloride, phosgene or oxalyl chloride.

The reaction with one of the imide-halide-forming agents mentioned is usually carried out in the presence of a suitable base, especially of an organic base, above all of a tertiary amine, for example a tertiary aliphatic monoamine or diamine, such as a tri-lower alkylamine, for example trimethylamine, triethylamine or N-ethyl-N,N-diisopropylamine, also a N,N,N',N'-tetra-lower alkyl-lower alkylenediamine, for example N,N,N',N'-tetramethyl-1,5-pentylenediamine or N,N,N',N'-tetramethyl-1,6-hexylenediamine, a monocyclic or bicyclic monoamine or diamine, such as a N-substituted, for example N-lower alkylated, alkyleneamine, azaalkyleneamine or oxaalkyleneamine, for example N-methyl-piperidine or N-methyl-morpholine, as well as 2,3,4,6,7,8-hexahydro-pyrrolo[1,2-a]pyrimidine (diazabicyclononene; DBN), or a tertiary aromatic amine such as a di-lower alkylaniline, for example N,N-dimethylaniline, or above all a tertiary heterocyclic, monocyclic or bicyclic, base, such as quinoline or isoquinoline, especially pyridine, preferably in the presence of a solvent, such as an optionally halogenated, for example chlorinated, aliphatic or aromatic hydrocarbon, for example methylene chloride. It is possible to use approximately equimolar amounts of the imide-halide-forming agent and of the base; the latter can however also be present in more than or less than equimolar amount, for example in about 0.2-fold to about 1-fold amount or in, up to about 10-fold, in particular about 3-fold to 5-fold, excess.

The reaction with the imide-halide-forming agent is preferably carried out with cooling, for example at temperatures of about −50° to about +10° C, but it is also possible to work at higher temperatures, that is to say, for example, up to about 75° C, if the stability of the starting substances and of the products permits a higher temperature.

The imide-halide product which is usually further processed without isolation, is reacted according to the process with an alcohol, preferably in the presence of one of the above-mentioned bases, to give the imino-ether. Examples of suitable alcohols are aliphatic as well as araliphatic alcohols, above all optionally substituted, such as halogenated, for example chlorinated, lower alkanols or lower alkanols possessing additional hydroxyl groups, for example ethanol, propanol or butanol but especially methanol, also 2-halogeno-lower alkanols, for example 2,2,2-trichloroethanol or 2-bromoethanol, and optionally substituted phenyl-lower alkanols, such as benzyl alcohol. Usually an excess, for example up to about 100-fold excess, of the alcohol is employed and the reaction is preferably carried out with cooling, for example at temperatures of about −50° to about 10° C.

The imino-ether product can advantageously be split without isolation. The splitting of the imino-ether can be achieved by treatment with a suitable hydroxy compound, preferably by means of hydrolysis, and also by alcoholysis, and the latter can take place directly following the formation of the imino-ether, if an excess of the alcohol is used. Preferably, water or an alcohol, especially a lower alkanol, for example methanol, or an aqueous mixture of an organic solvent, such as an alcohol, is used. The reaction is usually carried out in an acid medium, for example at a pH value of about 1 to about 5 which can, if necessary, be obtained by adding a basic agent, such as an aqueous alkali metal hydroxide, for example sodium hydroxide or potassium hydroxide, or an acid, for example a mineral acid, or an organic acid, such as hydrochloric acid, sulphuric acid, phosphoric acid, fluoroboric acid, trifluoroacetic acid or p-toluenesulphonic acid.

The three-stage process for splitting off an acyl group, described above, is advantageously carried out without isolation of the imide-halide and imino-ether intermediate products, usually in the presence of an organic solvent which is inert towards the reactants, such as an optionally halogenated hydrocarbon, for example methylene chloride, and/or in an inert gas atmosphere, such as a nitrogen atmosphere.

Certain acyl radicals $R_1^A$ of an acylamino grouping in compounds obtainable according to the invention such as, for example, the 5-amino-5-carboxy-valeryl radical, wherein carboxyl is optionally protected, for example by esterification, especially by diphenylmethyl, and/or the amino group is optionally protected, for example by acylation, especially by an acyl radical of an organic carboxylic acid, such as halogeno-lower alkanoyl, such as dichloroacetyl, or phthaloyl, can also be split off by treatment with a nitrosilylating agent, such as nitrosyl chloride, with a carbocyclic arenediazonium salt, such as benzenediazonium chloride, or with an agent which releases positive halogen, such as N-halogeno-amide or -imide, for example N-bromosuccinimide, preferably in a suitable solvent or solvent mixture, such as formic acid, together with a nitro- or cyano-lower alkane, and treatment of the reaction product with a hydroxylic agent, such as water or a lower alkanol, for example methanol or, if in the 5-amino-5-carboxy-valeryl radical $R_1^A$ the amino group is unsubstituted and the carboxyl group is protected, for example by esterification, and $R_1^b$ preferably represents an acyl radical but can also denote hydrogen, by leaving the substance to stand in an inert solvent, such as dioxane or a halogenated aliphatic hydrocarbon, for example methylene chloride and, if necessary, working up the free or monoacylated amino compound according to methods which are in themselves known.

A formyl group $R_1^A$ can also be split off by treatment with an acid agent, for example p-toluenesulphonic acid or hydrochloric acid, a weakly basic agent, for example dilute ammonia, or a decarbonylating agent, for example tris(triphenylphosphine)-rhodium chloride.

A triarylmethyl group, such as the trityl group $R_1^4$, can be split off, for example, by treatment with an acid agent, such as a mineral acid, for example hydrochloric acid.

The oxidative splitting off of the methylene group in compounds of the formula XII to form an oxo group in the 3-position of the cepham ring skeleton is preferably carried out by forming an ozonide compound by treatment with ozone. Herein, ozone is usually employed in the presence of a solvent, such as an alcohol, for example a lower alkanol, such as methanol or ethanol, a ketone, for example a lower alkanone, such as acetone, an optionally halogenated aliphatic, cycloaliphatic or aromatic hydrocarbon for example a halogeno-lower alkane, such as methylene chloride or carbon tetrachloride, or a solvent mixture, including an aqueous mixture, and with cooling or slight warming, for example at temperatures of about −90° to about +40° C.

An ozonide formed as an intermediate product is split by reduction, for which it is possible to use catalytically activated hydrogen, for example hydrogen in the presence of a heavy metal hydrogenation catalyst, such as a nickel catalyst or a palladium catalyst, preferably on a suitable carrier, such as calcium carbonate or charcoal, or chemical reducing agents, such as reducing heavy metals, including heavy metal alloys or amalgams, for example zinc, in the presence of a hydrogen donor, such as an acid, for example acetic acid, or an alcohol for example a lower alkanol, reducing inorganic salts, such as alkali metal iodides, for example sodium iodide, in the presence of a hydrogen donor, such as an acid, for example acetic acid, or reducing organic compounds, such as formic acid, a reducing sulphide compound such as a di-lower alkylsulphide, for example dimethylsulphide, a reducing organic phosphorus compound, such as a phosphine, which can optionally contain substituted aliphatic or aromatic hydrocarbon radicals as substituents, such as tri-lower alkyl-phosphines, for example tri-n-butylphosphine, or triarylphosphines, for example triphenylphosphine, also phosphites which contain optionally substituted aliphatic hydrocarbon radicals as substituents, such as tri-lower alkylphosphites, usually in the form of corresponding alcohol adduct compounds, such as trimethylphosphite, or phosphorous acid triamides which contain optionally substituted aliphatic hydrocarbon radicals as substituents, such as hexa-lower alkylphosphorous acid triamides, such as hexamethyl phosphorous acid triamide, the latter preferably in the form of a methanol adduct, or tetracyanoethylene. The splitting of the ozonide, which is usually not isolated, is normally carried out under the conditions which are employed for its manufacture, that is to say in the presence of a suitable solvent or solvent mixture, and with cooling or slight warming.

Depending on how the oxidation reaction is carried out, a 3-oxo-cepham compound of the formula (XIII)

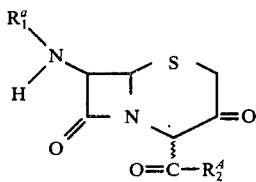

(XIII)

or the corresponding 1-oxide or a mixture of the two compounds is obtained. Such a mixture can be separated into the 3-oxo-cepham compound of the formula XII and the corresponding 1-oxide and be used as such, or can be oxidised to the pure 1-oxide.

A mixture of a 3-oxo-cepham compound of the formula XIII with the corresponding 1-oxide can be separated into the individual components in the usual manner, for example by fractional crystallisation or by chromatography (for example column chromatography or thin layer chromatography).

It is furthermore also possible to oxidise a mixture of a 3-oxo-cepham compound of the formula XIII and a 1-oxide thereof, directly to the 1-oxide of a 3-oxo-cepham compound employing the oxidising agents described above for the manufacture of 1-oxide compounds.

A compound of the formula XIII or a 1-oxide thereof, wherein $R_1{}^a$ is hydrogen, and wherein the 3-oxo group is protected, for example in the form of a functionally modified enol group, such as a silylated, for example trimethylsilylated, or stannylated enol group, can be acylated with an acid of the formula (IIIa) or with a reactive derivative thereof to give a starting compound of the formula II or a 1-oxide thereof. The acylation is carried out according to the methods described for the acylation of compounds of the formula IIa or IIb to the compounds of the formula IA or IB.

A starting compound of the formula IIa, or a 1-oxide thereof, or of the formula IIb, or a salt thereof can be obtained by converting a compound of the formula XIII, wherein $R_1{}^a$ is hydrogen or an amino protective group $R_1{}^A$, or a corresponding enol or a 1-oxide thereof, into an enol derivative having a functionally modified hydroxyl group of the formula —O—$R_3$ in the 3-position, of the formula

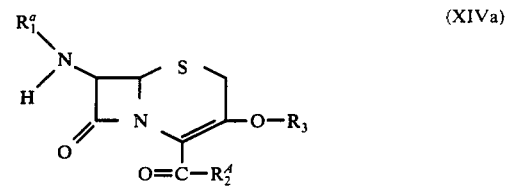

(XIVa)

or of the formula

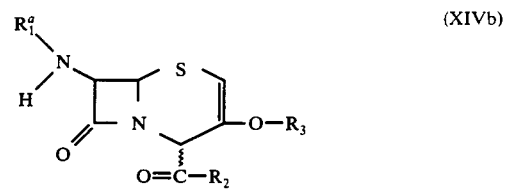

(XIVb)

or into a 1-oxide thereof, and splitting of an amino protective group $R_1{}^A$, and if desired splitting of the carboxyl protecting group in the group —C(=O)—$R_2{}^A$ to give a free carboxyl group.

The conversion of a compound of the formula (XIII) into a compound of the formula XIVa or XIVb out in analogy to the methods described for the conversion of a compound of the formula II into a compound of the formula IA or IB.

The splitting off of the amino protective group $R_1{}^A$ in a compound of the formula XIVa or XIVb can be achieved according to the methods described for the compounds of the formula XII, wherein the amino protective group $R_1{}^A$ is replaced by hydrogen.

The splitting off of the carboxyl protecting group —C(=O)—$R_2{}^A$ to give a free carboxyl group and any other optional modification, such as reducing an obtained 1-oxide or oxidising a compound of the formula IIa to give a 1-oxide thereof or transformation of a compound of the formula IIb into a compound of the formula IIa, or salt formation can be carried out in a manner known per se, and in analogy to processes described hereinbefore.

The pharmacologically usable compounds of the present invention can, for example, be used for the manufacture of pharmaceutical preparations which contain an effective amount of reactive substance together with, or mixed with, inorganic or organic, solid or liquid, pharmaceutically usable excipients which are suitable for enteral administration or for parenteral administration. Thus, tablets or gelatine capsules are used which contain the active compound together with diluents, for example lactose, dextrose, sucrose, mannitol, sorbitol, cellulose and/or glycine, and lubricants, for example silica, talc, stearic acid or salts thereof, such as magnesium stearate or calcium stearate, and/or polyethylene glycol; tablets also contain binders, for example magnesium aluminium silicate, starches, such as corn starch, wheat starch, rice starch or arrowroot starch, gelatine, tragacanth, methylcellulose, sodium carboxymethylcellulose and/or polyvinylpyrrolidone and, if desired, disintegrating agents, for example starches, agar, alginic acid or a salt thereof, such as sodium alginate, and/or effervescent mixtures, or adsorbents, dyestuffs, flavouring substances and sweeteners. Furthermore, the new pharmacologically active compounds can be used in the form of injectable preparations, for example preparations which can be administered intravenously, or of infusion solutions. Such solutions are, preferably, isotonic aqueous solutions or suspensions and these can, for example, be manufactured before use from lyophilised preparations which contain the active substance by itself or together with an excipient, for example mannitol. The pharmaceutical preparations can be sterilised and/or contain auxiliaries, for example preservatives, stabilisers, wetting agents or emulsifiers, solubilising agents, salts for regulating the osmotic pressure and/or buffers. The present pharmaceutical preparations which can, if desired, contain further pharmacologically valuable substances, are manufactured in a manner which is in itself known, for example by means of conventional mixing, granulating, dragee-making, dissolving or lyophilising processes, and contain from about 0.1% to 100%, especially from about 1% to about 50%, of lyophilised products or up to 100% of the active substance.

In the context of the present description, the organic radicals described as "lower" contain, unless expressly defined, up to 7, preferably up to 4, carbon atoms; acyl radicals contain up to 20, preferably up to 12, and above all up to 7, carbon atoms.

The examples which follow serve to illustrate the invention.

EXAMPLE 1 a. A solution, cooled to 0° C, of 0.253 g of D-$\alpha$-tert.-butoxycarbonylamino-$\alpha$-(1,4-cyclohexadienyl)-acetic acid in 75 ml of methylene chloride is stirred for 30 minutes in 0.097 ml of N-methyl-morpholine and 0.129 ml of chloroacetic acid isobutyl ester under a nitrogen atmosphere and the mixture is then cooled to $-10°$ C and is successively treated with 0.30 g of 7$\beta$-amino-3-methoxy-3-cephem-4-carboxylic acid diphenylmethyl ester and 0.085 g of N-methyl-morpholine. The reaction mixture is stirred for 30 minutes at $-10°$ C and for 30 minutes at 0° C, 30 ml of water are added, and the pH value is adjusted to 7.9 by adding 40% strength aqueous dipotassium hydrogen phosphate solution. The phases are separated, the aqueous solution is extracted with methylene chloride and the combined organic solutions are washed with a saturated aqueous sodium chloride solution, dried over sodium sulphate and evaporated under reduced pressure. The residue is purified by means of preparative layer chromatography (silica gel; system: diethyl ether; identification with ultraviolet light, $\lambda = 254$ m$\mu$; Rf$\sim$0.39). 7$\beta$-[D-$\alpha$-tert.-Butoxycarbonylamino-$\alpha$-(1,4-cyclohexadienyl)-acetylamino]-3-methoxy-3-cephem-4-carboxylic acid diphenylmethyl ester, which according to thin layer chromatography is a single substance, is obtained as an amorphous product, thin layer chromatogram (silica gel; identification with diethyl ether): Rf$\sim$0.39 (system: diethyl ether); $[\alpha]_D^{20} = +1° \pm 1°$ (c = 0.745 in chloroform); ultraviolet absorption spectrum (in 95% strength aqueous ethanol): $\lambda_{max} = 263$ m$\mu$ ($\epsilon = 6,700$) and $\lambda_{shoulder} = 280$ m$\mu$ ($\epsilon = 6,300$); infrared absorption spectrum (in methylene chloride): characteristic bands at 2.96 $\mu$, 5.64 $\mu$, 5.86 $\mu$, 5.90 $\mu$ (shoulder), 6.27 $\mu$ and 6.73 $\mu$.

b. If, in the above process, 0.09 g of D-$\alpha$-tert.-butoxycarbonylamino-$\alpha$-(1,4-cyclohexadienyl)-acetic acid, 0.038 ml of N-methyl-morpholine and 0.052 ml of chloroformic acid isobutyl ester are used and the mixture is stirred for 30 minutes at $-15°$ C under a nitrogen atmosphere, then treated with 0.125 g of 7$\beta$-amino-3-methoxy-3-cephem-4-carboxylic acid diphenylmethyl ester and 0.035 ml of N-methyl-morpholine, stirred for 30 minutes at $-10°$ C and for 30 minutes at 0° C and worked up as described above, a crude product is obtained, which is purified by means of preparative layer chromatography (silica gel; system: diethyl ether; identification with ultraviolet light, $\lambda = 254$ $\mu$). At Rf$\sim$0.51, 7$\beta$-[D-$\alpha$-tert.-butoxycarbonylamino-(1,4-cyclohexadienyl)-acetylamino]-3-methoxy-2-cephem-4$\alpha$-carboxylic acid diphenylmethyl ester is thus obtained, melting point = 153°–154° C after crystallisation from a mixture of methylene chloride and pentane; thin layer chromatogram (silica gel; identification with iodine): Rf$\sim$0.51 (system: diethyl ether); $[\alpha]_D^{20} = +176° \pm 1°$ (c = 0.541 in chloroform); ultraviolet absorption spectrum (in 95% strength aqueous ethanol): $\lambda_{max} = 257$ m$\mu$ ($\epsilon = 3,600$); and infrared absorption spectrum (in methylene chloride): characteristic bands at 2.96 $\mu$, 5.64 $\mu$, 5.76 $\mu$, 5.92 $\mu$, 6.18 $\mu$ and 6.75 $\mu$; whilst at Rf$\sim$0.39 7$\beta$-[D-$\alpha$-tert.-butoxycarbonyl-amino-$\alpha$-(1,4-cyclohexadienyl)-acetylamino]-3-methoxy-3-cephem-4-carboxylic acid diphenylmethyl ester is obtained, which is identical with the product obtainable according to the process described above.

EXAMPLE 2

A mixture of 0.200 g of 7$\beta$-[D-$\alpha$-tert.-butoxycarbonylamino-$\alpha$-(1,4-cyclohexadienyl)-acetylamino]-3-methoxy-3-cephem-4-carboxylic acid diphenylmethyl ester, 0.5 ml of anisole and 10 ml of pre-cooled trifluoroacetic acid is stirred for 15 minutes at 0° C and subsequently mixed with 50 ml of cold toluene and evaporated under reduced pressure. The residue is stirred with diethyl ether and the pulverulent precipitate is filtered off and dried. The salt, thus obtained, of 7$\beta$-[D-$\alpha$-amino-$\alpha$-(1,4-cyclohexadienyl)-acetylamino]-3-methoxy-3-cephem-4-carboxylic acid with trifluoroacetic acid is dissolved in about 6 ml of water, the pH value of the solution is adjusted to 1.5 by adding 2 N hydrochloric acid, the aqueous solution is washed with 20 ml of ethyl acetate and its pH value is adjusted to 5.0 by dropwise addition of a 20% strength solution of triethylamine in methanol. It is diluted with 20 ml of acetone and 10 ml of diethyl ether and the mixture is left to stand for 16 hours at 0° C. The resulting precipitate is filtered off, washed with acetone and diethyl ether and dried. 7$\beta$-[D-$\alpha$-amino-$\alpha$-(1,4-cyclohexadienyl)-acetylamino]-3-methoxy-3-cephem-4-carboxylic acid is thus obtained in the form of the internal salt, melting point 170° C (with decomposition); thin layer chromatogram (silica gel; identification with iodine): Rf$\sim$0.26 (system: n-butanol/acetic acid/water, 67:10:23) and Rf$\sim$0.58 (system: isopropanol/formic acid/water, 77:4:19); ultraviolet absorption spectrum: $\lambda_{max} = 267$ m$\mu$ ($\epsilon = 6,100$) in 0.1 N hydrochloric acid, and $\lambda_{max} = 268$ m$\mu$ ($\epsilon = 6,600$) in 0.1 N aqueous sodium bicarbonate solution.

EXAMPLE 3

A suspension of 30.64 g (0,2 mol) of D-$\alpha$-amino-$\alpha$-(1,4-cyclohexadienyl)-acetic acid in 600 ml of methylene chloride is cooled under a stream of argon to 6° C, whereupon hydrogen chloride is passed in for about 30 minutes until the mixture is saturated. Phosphorpentachlorid (62,4 g; 0,3 mol) is added in two portions. The mixture is stirred for 2 hours at 6°–8° C. The colorless precipitate is filtered off under nitrogen and exclusion of moisture, washed with methylene chloride and dried for 18 hours at 0,05 mm Hg at roomtemperature to give D-α-amino-α-(1,4-cyclohexadienyl)-acetylchlorid hydrochloride in form of colorless crystals.

A suspension of 37,3 g (0,1 mol) of 7β-amino-3-methoxy-3-cephem-4-carboxylic acid hydrochloride dioxanate in 500 ml methylene chloride is stirred for 15 minutes at roomtemperature under an argon atmosphere and treated with 57,2 ml (0,23 mol) of bis-(trimethylsilyl)-acetamide. After 45 minutes the faintly yellow slightly turbid solution is cooled to 0° C and treated within 10 minutes with 31.2 g (0,15 mol) of D-α-amino-α-(1,4-cyclohexadienyl)-acetyl chloride hydrochloride. Thirty minutes thereafter 15 ml (ca. 0,21 mol) of propylene oxide is added and the mixture is further stirred for 1 hour at 0° C. A cooled mixture of 20 ml of absolute methanol in 200 ml of methylene chloride is added within 30 minutes, after another 30 minutes the precipitate is filtered off under exclusion of moisture, washed with methylene chloride and dried under reduced pressure at roomtemperature. The obtained hygroscopic crystals of the hydrochloride of 7β-[D-α-amino-α-(1,4-cyclohexadienyl)-acetylamino]-3-methoxy-3-cephem-4-carboxylic acid are stirred into 200 ml of ice water and the milky solution treated with about 66 ml of cold 2 N sodium hydroxide solution until pH 3.5 is reached. The solution is clarified by filtration through diatomaceous earth, washed with ice water, cooled to 0° C and treated with 20 ml of 2N sodium hydroxide solution until pH 5,7 is reached. A second filtration through a glasfilter frit results in a clear solution which is treated with aceton (800 ml) at 0°. The crystals are filtered washed with acetone: water (2:1), acetone and diethyl ether and dried for 20 hours at room temperature and 0,05 mm Hg to give the 7β-[D-α-amino-α-(1,4-cyclohexadienyl)-acetylamino]-3-methoxy-3-cephem-4-carboxylic acid dihydrate; $[\alpha]_D = +87 \pm 1°$ (c = 1,093; 0,1N HCl); UV-spectrum: $\lambda_{max} = 268$ mμ (ε = 6700) in 0,1N HCl; $\lambda_{max} = 269$ mμ (ε = 7100) in 0,1N NaHCO$_3$ solution.

EXAMPLE 4

A solution prepared by mixing 18,25 ml (0,02 ml) of a 1,1M methanolic solution of sodium methoxid and 20 ml of absolute methanol is treated at roomtemperature under nitrogen and exclusion of moisture with 3,06 g (0,02 mmol) of D-α-amino-α-1,4-cyclohexadienyl-acetic acid and 10 minutes thereafter with 2,6 ml (0,024 mol) of methyl acetoacetate. The mixture is refluxed during 1 hour and then evaporated under vacuum. The residue is treated three times with toluene and evaporated again to remove the rest of the methanol. The foamy residue is dissolved in ca. 50 ml of methylene chloride, filtered, again evaporated and dried for 18 hours at 0,01 mm Hg and roomtemperature to give a light yellow powder of D-α-(1-methoxy-croton-3-ylamino)-α-1,4-cyclohexadienyl-acetic acid sodium salt, mp 241°–244° C (decomposition).

A solution of 1.97 g (7,2 mmol) of the obtained sodium salt in 40 ml of acetonitrile is cooled to −10° C and treated with a catalytic amount of N,N-dimethylbenzylamine and 0,95 ml (7,2 mmol) of chloroformic acid isobutylester under an argon atmosphere. The mixture is stirred for 25 minutes and treated at −10° C with a solution of 7β-amino-3-methoxy-3-cephem-4-carboxylic acid trimethylsilyl ester, obtained by stirring for 60 minutes at roomtemperature a suspension of 2,29 g (6 mmol) of 7β-amino-3-methoxy-3-cephem-4-carboxylic acid hydrochloride dioxanate in 60 ml of methylene chloride together with 3.1 ml (12,6 mmol) of bis-(trimethylsilyl)-acetamide. The reaction mixture is stirred for 2 hours at 0° C and the solvents are evaporated under vacuum. The oily residue is dissolved in 60 ml of acetonitrile: water 2:1, acidified with 3,5 ml of 2N hydrochloric acid up to pH 1,0 and stirred for 2 hours at 0° C. After addition of 1 N sodium hydroxide solution until pH 3,5 is reached, the solution is evaporated, the residue dissolved in 16 ml of water and extracted with ethylacetate. The aqueous phase is cooled to 0° C, treated with 2 N sodium hydroxide solution until pH 5,7 is reached and treated with 40 ml of acetone. The crystals are filtered off washed with acetone: water 2:1, acetone and diethyl ether and dried for 18 hours at 0,05 mmHg to give the 7β-[D-α-amino-α-(1,4-cyclohexadienyl)-acetylamino]-3-methoxy-3-cephem-4-carboxylic acid monohydrate; UV-spectrum: $\lambda_{max}$: 267 mμ (ε = 6300) in 0,1N HCl.

EXAMPLE 5

A solution of 615 mg of 7β-[D-α-tert.-butoxycarbonylamino-α-(1,4-cyclohexadienyl)-acetylamino]-3-hydroxy-3-cephem-4ξ-carboxylicacid diphenylmethyl ester in 12 ml methanol is treated at 0° C with an excess of diazomethane in diethyl ether and stirred for 30 minutes at this temperature. The reaction mixture is treated with 1-2 ml of acetic acid and evaporated under reduced pressure. The residue is chromatographed on thick silica gel plates with toluene/ethyl acetate 1:1. Elution of the zone visible at UV-light of 254 nm results in the 7β-[D-α-tert.-butoxycarbonylamino-α-(1,4-cyclohexadienyl)-acetylamino]-3-methoxy-3-cephem-4-carboxylic acid diphenylmethyl ester, which is pure according to thin layer chromatography, and is obtained as an amorphous product; thin layer chromatogram (silica gel; identification with diethyl ether): Rf~0,39 (system: diethyl ether); $[\alpha]_D^{20} = \pm 1° \pm 1°$ (c = 0,745 in chloroform); ultraviolet absorption spectrum (in 95% strength aqueous ethanol): $\lambda_{max} = 263$ mμ (ε = 6,700) and $\lambda_{shoulder} = 280$ mμ (ε = 6,300); infrared absorption spectrum (in methylene chloride): characteristic bands at 2,96 μ, 5,64 μ, 5,86 μ, 5,90 μ (shoulder) 6,27 μ and 6,73 μ.

The starting materials can be manufactured as follows:

EXAMPLE 6 a. A solution of 11.82 g of the crude sodium salt of 3-hydroxymethyl-7β-phenylacetylamino-3-cephem-4-carboxylic acid (manufactured by enzymatic desacetylation of the sodium salt of 3-acetoxymethyl-7β-phenylacetylamino-3-cephem-4-carboxylic acid with the aid of a purified enzyme extract from *Bacillus subtilis*, strain ATCC 6,633, and subsequent lyophilisation of the reaction solution) in 200 ml of water is covered with 400 ml of ethyl acetate and acidified to a pH value of 2 with concentrated aqueous phosphoric acid. The aqueous phase is separated off and twice re-extracted with 150 ml of ethyl acetate at a time. The combined organic extracts are washed four times with 50 ml of water at a time, dried over magnesium sulphate and then concentrated to about 400 ml. Excess diphenyldiazomethane is added to the solution, which is left to stand for 3 hours at room temperature, and the granular crystalline precipitate is then filtered off. The filtrate is concentrated to about 200 ml, cyclohexane is added whilst warm and after cooling to room temperature the mixture is left to stand for some time at about 4° C. The precipitate is filtered off and recrystallised from a mixture of acetone and cyclohexane; the 3-hydroxymethyl-7β-phenylacetylamino-3-cephem-4-carboxylic acid diphenylmethyl ester thus obtained melts at 176°–176.5° C (uncorrected); $[\alpha]_D^{20} = -6° \pm 1°$ (c = 1.231% in chloroform); thin layer chromatogram (silica gel; detection with iodine vapour or ultraviolet light, $\lambda_{254\ m\mu}$); Rf = 0.42 (system: chloroform/acetone; 4:1), Rf = 0.43 (system: toluene/acetone, 2:1), and Rf = 0.41 (system: methylene chloride/acetone, 6:1).

b. 1.03 g of 3-hydroxymethyl-7β-phenylacetylamino-3-cephem-4-carboxylic acid diphenylmethyl ester and 1.05 g of N-methyl-N,N'-dicyclohexylcarbodiimidium iodide are dissolved in 25 ml of absolute tetrahydrofurane under a nitrogen atmosphere and warmed at 35° C for 1 hour. Thereafter, a further 1.05 g of N-methyl-N,N'-dicyclohexylcarbodiimidium iodide, in 15 ml of absolute tetrahydrofurane, is added and the mixture is left to stand for 17 hours at room temperature under a nitrogen atmosphere. The reaction mixture is freed of the solvent on a rotary evaporator under reduced pressure. The residue is taken up in methylene chloride and filtered through a column of 50 g of silica gel (with addition of 10% of distilled water); the column is rinsed with 4 portions of methylene chloride, each of 100 ml. The eluate is concentrated to a small volume and chromatographed on a silica gel column (90 g; deactivated by adding 10% of distilled water). Non-polar impurities are eluted with a total of 900 ml of a 3:7 mixture of toluene and methylene chloride. Elution with 2 portions of methylene chloride, each of 200 ml, yields 3-iodomethyl-7β-phenylacetylamino-3-cephem-4-carboxylic acid diphenylmethyl ester; the fractions which according to a thin layer chromatogram are a single substance are lyophilised from benzene. Infrared absorption spectrum (in methylene chloride): characteristic bands at 3.00 μ, 5.62 μ, 5.82 μ, 5.95 μ, 6.70 μ, 7.32 μ and 8.16 μ.

The iodination reagent used above can be manufactured as follows:

bi. 42 g of freshly distilled N,N'-dicyclohexylcarbodiimide are dissolved in 90 ml of methyl iodide in a 250 ml round flask equipped with a magnetic stirrer and reflux condenser and fitted nitrogen bulb, at room temperature under a nitrogen atmosphere, and the colourless reaction mixture is stirred for 72 hours at a bath temperature of 70° C. At the end of the reaction time, the excess methyl iodide is distilled from the solution, which is now red-brown, under reduced pressure and the viscous red-brown residue is dissolved in 150 ml of absolute toluene at 40° C. The crystal mass, which crystallises out spontaneously within a few hours, is separated from the mother liquor with the aid of a glass suctiion filter with fitted nitrogen bulb, whilst excluding air, the reaction vessel is rinsed three times with 25 ml of absolute, ice-cold toluene at a time and the same toluene is used in order to wash the slightly yellowish crystal mass on the glass suction filter until it is colourless. After drying for 20 hours at 0.1 mm Hg and room temperature, the N-methyl-N,N'-dicyclohexylcarbodiimidium iodide is obtained in the form of colourless crystals, melting point 111°–113° C; infrared absorption spectrum (in chloroform): characteristic bands at 4.72 μ and 6.00 μ.

c. A solution of 0.400 g of 3-iodomethyl-7β-phenylacetylamino-3-cephem-4-carboxylic acid diphenylmethyl ester in 15 ml of 90% strength aqueous acetic acid is cooled to 0° C in an ice bath and 2.0 g of zinc dust are added in portions whilst stirring well. After a reaction time of 30 minutes at 0° C the unreacted zinc dust is filtered off by means of a suction filter covered with a layer of diatomaceous earth; the filter residue is repeatedly suspended in fresh methylene chloride and again filtered. The combined filtrates are concentrated under reduced pressure, mixed with absolute toluene and evaporated to dryness under reduced pressure. The residue is taken up in 50 ml of methylene chloride and 30 ml of an 0.5 molar aqueous dipotassium hydrogen phosphate solution, whilst stirring; the aqueous phase is separated off, re-extracted with two portions of methylene chloride, each of 30 ml, and discarded. The organic extracts are repeatedly washed with a saturated aqueous sodium chloride solution, dried over magnesium sulphate and evaporated under reduced pressure. The residue is chromatographed on a column of 22 g of silica gel (with addition of 10% of water). The 3-methylene-7β-phenylacetylamino-cepham-4α-carboxylic acid diphenylmethyl ester is eluted with methylene chloride, and with methylene chloride containing 2% of methyl acetate, and is crystallised from a mixture of methylene chloride and hexane, melting point 144°–147° C; $[\alpha]_D^{20} = -18° \pm 1°$ (c = 0.715 in chloroform); ultraviolet absorption spectrum (in 95% strength aqueous ethanol): $\lambda_{max}$ = 254 mμ (ε= 1,540) and 260 mμ (ε= 1,550); infrared absorption spectrum (in methylene chloride): characteristic bands at 2.94 μ, 5.65 μ, 5.74 μ, 5.94 μ, 6.26 μ and 6.67 μ.

d. A solution, cooled to −15° C, of 2.0 g of 3-methylene-7β-phenylacetylamino-cepham-4α-carboxylic acid diphenylmethyl ester in 80 ml of absolute methylene chloride is mixed with 3.2 ml of absolute pyridine and 32 ml of an 8% strength solution of phosphorus pentachloride in methylene chloride and stirred for one hour under a nitrogen atmosphere at a temperature between −10° and −5° C. The reaction mixture is then cooled to −25° C, mixed with 25 ml of absolute methanol and stirred for one hour at −10° C and then for 1.5 hours at room temperature. 80 ml of an 0.5 molar aqueous solution of potassium dihydrogen phosphate are then added, the pH value is adjusted to 2 with 20% strength aqueous phosphoric acid and the mixture is stirred for 30 minutes at room temperature.

The organic phase is separated off; the aqueous phase is twice re-extracted with 150 ml of methylene chloride at a time and the organic solutions are combined, dried over sodium sulphate and evaporated. The oily residue is taken up in 25 ml of ethyl acetate and a solution of 1.14 g of 4-methylphenylsulphonic acid monohydrate in 25 ml of ethyl acetate is added at 0° C. A voluminous precipitate separates out, which is filtered off, rinsed with cold ethyl acetate and diethyl ether, dried and recrystallised, from a mixture of methylene chloride and diethyl ether. The 4-methylphenylsulphonate of 7β-amino-3-methylenecepham-4α-carboxylic acid diphenylmethyl ester is thus obtained in the form of colourless needles, melting point 153°–155° C; $[\alpha]_D = -14° \pm 1°$ (c = 0.97 in methanol); ultraviolet absorption spectrum (in ethanol): $\lambda_{max}$ = 257 μ (ε= 1,500); infrared absorption spectrum (in methylene chloride): characteristic bands at 3.5 μ, 5.60 μ, 5.73 μ, 8.50 μ, 9.68 μ and 9.92 μ.

e. A stream of oxygen and ozone (containing 0.35 mmol of ozone per minute) is passed for 4 minutes through a solution, cooled to −60° C, of 0.553 g of the 4-methylphenylsulphonate of 7β-amino-3-methylene-cepham-4α-carboxylic acid diphenylmethyl ester in 50 ml of methanol. After a further 5 minutes, the pale blue-coloured solution is treated with 0.3 ml of dimethyl sulphide. The mixture is stirred for 15 minutes at −70° C, for 1 hour at −12° C and for 1 hour in an ice bath and is then evaporated. The residue is taken up in a small amount of methylene chloride, diethyl ether is then added until the mixture turns cloudy, and the mixture is left to stand. The microcrystalline, reddish-coloured pulverulent precipitate is filtered off and yields the 4-methylphenylsulphonate of 7β-amino-cepham-3-one-4α-carboxylic acid diphenylmethyl ester which is mainly present in the enol form as the 4-methylphenyl-sulphonate of 7β-amino-3-cephem-3-ol-4-carboxylic acid diphenylmethyl ester, melting point = 143°–145° C (with decomposition); thin layer chromatogram (silica gel) Rf ∼0.28 (system: ethyl acetate/pyridine/water, 85:10:5); ultraviolet absorption spectrum (in ethanol): $\lambda_{max} = 262$ mμ ($\epsilon = 3,050$) and 282 mμ ($\epsilon = 3,020$); infrared absorption spectrum (in methylene chloride): characteristic bands at 5.58 μ, 5.77 μ (shoulder), 6.02 μ and 6.22 μ.

f. A solution of 0.50 g of the 4-methylphenylsulphonate of 7β-amino-cepham-3-one-4ξ-carboxylic acid diphenylmethyl ester, which is predominantly present in the enol form, that is to say as the 4-methylphenylsulphonate of 7β-amino-3-cephem-3-ol-4-carboxylic acid diphenylmethyl ester, in 25 ml of methanol, is treated, at 0° C with a solution of diazomethane in diethyl ether until the yellow colouration persists. The mixture is stirred for 10 minutes in an ice bath and is then evaporated. The residue is chromatographed on silica gel. Oily 7β-dimethylamino-3-methoxy-3-cephem-4-carboxylic acid diphenylmethyl ester is eluted with a 2:1 mixture of toluene and ethyl acetate, thin layer chromatogram (silica gel; development with iodine vapour): Rf∼0.39 (system: ethyl acetate); ultraviolet absorption spectrum (in ethanol): $\lambda_{max} = 265$ μ ($\epsilon = 6,100$); infrared absorption spectrum (in methylene chloride): characteristic bands at 3.33 μ, 5.63 μ, 5.81 μ and 6.23 μ.

Further elution with ethyl acetate yields oily 7β-amino-3-methoxy-3-cephem-4-carboxylic acid diphenylmethyl ester, thin layer chromatogram (silica gel; development with iodine vapour): Rf∼0.20 (system: ethyl acetate); ultraviolet absorption spectrum (in ethanol): $\lambda_{max} = 265$ μ ($\epsilon = 5,900$); infrared absorption spectrum (in methylene chloride): characteristic bands at 2.98 μ, 3.33 μ, 5.62 μ, 5.81 μ and 6.24 μ.

g. A solution of 2,17 g (4,16 mmol) of the 4-methylphenylsulphonic acid salt of 7β-amino-cepham-3-one-4ξ-carboxylic acid diphenylmethylester in 25 ml of methylene chloride is treated with 1,04 ml (4,16 mmol) bis-trimethylsilyl-acetamide and stirred at room temperature under nitrogen for 45 minutes (solution A).

A mixture of 1,47 g (5,83 mmol) of D-α-tert.-butyloxycarbonylamino-α-(1,4-cyclohexadienyl)-acetic acid and 24 ml methylene chloride of −20° C is treated with 0,65 ml of N-methyl-morpholine and 0,80 ml of chloroformic acid isobutylester and the solution is stirred for 45 minutes at −20° C under nitrogen (solution B).

Solution A is cooled to −20° C and solution B is added whereupon the combined solutions are stirred for 2½ hours at 0° C. The reaction mixture is washed with water and saturated aqueous sodium chloride solution, dried over sodium sulphate and evaporated under reduced pressure. The residue is chromatographed on 70 g of silica gel with toluene/ethyl acetate 4:1 to give 7β-[-α-tert.-butoxycarbonylamino-α-(1,4-cyclohexadienyl)-acetylamino[-3-hydroxy-3-cephem-4ξ-carboxylic-acid diphenylmethyl ester; Rf = 0,35 (silica gel; ethyl acetate); IR-spectrum (chloroform): bands at 3380; 1780; 1690; 1610; 1590; 1470 cm⁻¹.

h. A solution of 1g of the 4-methylphenyl-sulfonate of 7β-amino 3-methoxy-3-cephem-4α-carboxylic acid diphenylmethylester in 20 ml of methylenechloride is shaken with a phosphate buffer solution of pH 7–8. The organic phase is dried over sodiumsulfate, saturated with hydrogen chloride at 0° C and left to stand for 30 minutes at this temperature. The mixture is evaporated at low temperature in vacuum. The residue is dissolved in 4 ml of water and extracted with methylene chloride. The aqueous phase is treated with 40 ml of dioxan and the crystals of 7β-amino-3-methoxy-3-cephem-4-carboxylic acid hydrochloride dioxanate are filtered off and recrystallised from water and dioxan; mp. > 300° C; UV-spectrum (0,1 N sodiumbicarbonate): $\lambda_{max} = 270$ mμ ($\epsilon = 7600$), $[\alpha]_D^{20} = +134° \pm 1°$ (c = 1; 0,5 N sodiumbicarbonate).

i. A suspension of 1.65 g of 7β-amino-3-methoxy-3-cephem-4-carboxylic acid diphenylmethyl ester and 2 ml of anisole is mixed with 20 ml of pre-cooled trifluoroacetic acid and stirred for 15 minutes in an ice bath. It is diluted with 100 ml of cold toluene and the reaction mixture is evaporated under reduced pressure. The dark brown residue is dried under a high vacuum and stirred with diethyl ether; the precipitate is filtered off, washed with acetone and diethyl ether and dried. The salt, thus obtainable, of 7β-amino-3-methoxy-3-cephem-4-carboxylic acid and of trifluoroacetic acid is dissolved in 10 ml of water; the aqueous solution is twice washed with 10 ml of ethyl acetate at a time and brought to a pH of 4.5 by adding a 10% strength solution of triethylamine in methanol. The mixture is diluted with 10 ml of acetone and stirred for one hour at 0° C. The precipitate is filtered off, washed with a 1:2 mixture of acetone and diethyl ether and dried in a high vacuum and yields 7β-amino-3-methoxy-3-cephem-4-carboxylic acid in the form of the internal salt, thin layer chromatogram (silica gel): Rf∼0.16 (system: n-butanol/acetic acid/water, 67:10:23); ultraviolet absorption spectrum (in 0.1 N hydrochloric acid): $\lambda_{max} = 261$ mμ ($\epsilon = 5,400$).

The hydrochloride dioxanante of this compound can be obtained by treatment with hydrochloric acid and dioxan as described under Example 6h.

EXAMPLE 7

Dry ampoules or phials, containing 0.5 g of the internal salt of 3-methoxy-7β-[D-α-amino-α-(1,4-cyclohexadienyl)-acetylamino]-3-cephem-4-carboxylic acid are manufactured as follows:

| Composition (for 1 ampoule or phial) | |
| --- | --- |
| Internal salt of 3-methoxy-7β-D-α-amino-α-(1,4-cyclohexadienyl)-acetylamino]-3-cephem-4-carboxylic acid | 0.5 g |
| Mannitol | 0.05 g |

A sterile aqueous solution of the internal salt of 3-methoxy-7β-[D-α-amino-α-(1,4-cyclohexadienyl)-acetylamino[-3-cephem-4-carboxylic acid and of the mannitol is subjected to freeze-drying under aseptic conditions in 5 ml ampoules or 5 ml phials and the ampoules or phials are sealed and tested.

EXAMPLE 8

Capsules, containing 0,25 g of the internal salt of 3-methoxy-7β-[D-α-amino-α-(1,4-cyclohexadienyl)-acetylamino]-3-cephem-4-carboxylic acid are manufactured as follows:

| Composition (for 4,000 capsules): | |
|---|---|
| Internal salt of 3-methoxy-7β-[D-α-amino-α-(1,4-cyclohexadienyl)-acetylamino]-3-cephem-4-carboxylic acid | 250.000 g |
| Corn starch | 50.000 g |
| Polyvinylpyrrolidone | 15.000 g |
| Magnesium stearate | 5.000 g |
| Ethanol | q.s. |

The internal salt of 3-methoxy-7β-[D-α-amino-α-(1,4-cyclohexadienyl)-acetylamino]-3-cephem-4-carboxylic acid and the corn starch are mixed and moistened with a solution of polyvinylpyrrolidone in 50 g of ethanol. The moist mass forced through a sieve of 3 mm mesh width and dried at 45° C. The dry granules are forced through a sieve of 1 mm mesh width and mixed with 5 g of magnesium stearate. The mixture is filtered, in portions of 0,320 g, into push-fit capsules of size 0.

We claim:

1. An O-substituted 7β-amino-3-cepham-3-Ol-carboxylic acid compound of the formula

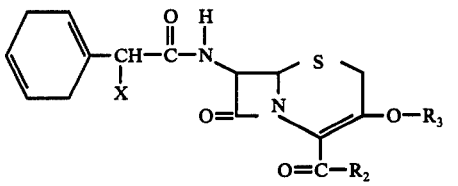

wherein X represents amino, $R_2$ represents hydroxyl or a group $R_2^A$ which together with the carbonyl grouping —C(=O)— forms a protected carboxyl group, and $R_3$ is lower alkyl, lower alkenyl, phenyl-lower alkyl, lower alkanoyl or lower alkoxycarbonyl, or pharmaceutically acceptable salts thereof.

2. A compound according to claim 1 of the formula IA, wherein X is amino, $R_2$ is hydroxyl and $R_3$ is lower alkyl, lower alkenyl, phenyl-lower alkyl, lower alkanoyl or lower alkoxycarbonyl, and pharmaceutically acceptable salts thereof.

3. A compound according to claim 1 of the formula IA, wherein X is amino, $R_2$ is hydroxy, and $R_3$ is lower alkyl, and pharmaceutically acceptable salts thereof.

4. A compound according to claim 1, which is a 7β-[D-α-amino-α-(1,4-cyclohexadienyl)-acetylamino]-3-lower alkoxy-3-cephem-4-carboxylic acid, wherein lower alkoxy contains up to 4 carbon atoms, and pharmaceutically acceptable salts thereof.

5. A compound according to claim 1, which is the 7β-[D-α-amino-α-(1,4-cyclohexadienyl)-acetylamino]-3-methoxy-3-cephem-4-carboxylic acid, a salt or a hydrate thereof.

6. The dihydrate or the monohydrate of the compound according to claim 5.

7. An O-substituted 7β-amino-3-cephem-3-ol-4-carboxylic acid compound of the formula

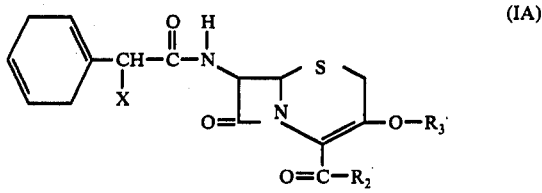

wherein X represents protected amino, $R_2$ represents hydroxyl or a group $R_2^A$ which together with the carbonyl grouping —C(=O)— forms a protected carboxyl group, and $R_3$ is lower alkyl, lower alkenyl, phenyl-lower alkyl, lower alkanoyl or lower alkoxycarbonyl, 1-oxides thereof or an O-substituted 7β-amino-2-cephem-3-ol-4-carboxylic acid compound of the formula

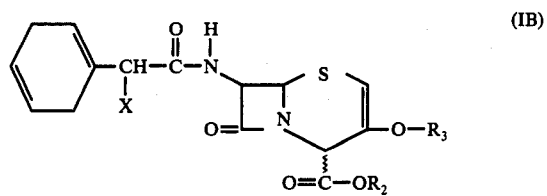

wherein X represents amino or protected amino, $R_2$ and $R_3$ have the above-mentioned meanings, or salts thereof.

8. A compound according to claim 7 of the formula IA, wherein X is lower alkoxycarbonylamino, 2-halogeno-lower alkoxycarbonylamino, phenyl-lower alkoxycarbonylamino, mono-lower-alkoxy-substituted phenyl-lower alkoxycarbonylamino, mono-nitro-substituted phenyl-lower alkoxycarbonylamino, tritylamino, nitrophenylthioamino, tritylthioamino, 2-propylidenamino or 2-propylidenamino substituted in 1-position by lower alkoxycarbonyl or lower alkanoyl, $R_2$ is hydroxyl, lower alkoxy, 2-halogeno-lower alkoxy, methoxy substituted by one phenylcarbonyl, one phenyl, one lower-alkoxy phenyl or one mono-nitrophenyl, methoxy substituted by two phenyl or by two lower alkoxy phenyl, or trilower alkylsilyloxy, and $R_3$ is lower alkyl, lower alkenyl, phenyl-lower alkyl, lower alkanoyl or lower alkoxycarbonyl, a 1-oxide of such compound of the formula IA, and salts thereof.

9. A compound according to claim 7 of the formula IA, wherein X is tert.-butyloxycarbonylamino, 2,2,2-trichloroethoxycarbonylamino, 4-methoxybenzyloxycarbonylamino, diphenylmethoxycarbonylamino or tritylamino, $R_2$ is 2,2,2-trichloroethoxy, 2-iodoethoxy, 2-chloroethoxy or 2-bromoethoxy, phenacyloxy, benzyloxy, methoxybenzyloxy, nitrobenzyloxy, diphenylmethoxy, 4,4'-dimethoxy-diphenylmethoxy, or trimethylsilyloxy, and $R_3$ is lower alkyl, and salts thereof.

10. A compound according to claim 7 of the formula IB, wherein X is lower alkoxycarbonylamino, 2-halogeno-lower alkoxycarbonylamino, phenyl-lower alkoxycarbonylamino, mono-lower-alkoxy-substituted phenyl-lower alkoxycarbonylamino, mono-nitro-substituted phenyl-lower alkoxycarbonylamino, tritylamino, nitrophenylthioamino, tritylthioamino, 2-propylidenamino or 2-propylidenamino substituted in 1-position by lower alkoxycarbonyl or lower alkanoyl, $R_2$ is hydroxyl, lower alkoxy, 2-halogeno-lower alkoxy, methoxy substituted by one phenylcarbonyl, one phenyl, one lower-alkoxy phenyl or one mono-nitrophenyl, methoxy substituted by two phenyl or by two lower alkoxy phenyl, or tri-lower alkylsilyloxy, and R₃ is lower alkyl, lower alkenyl, phenyl-lower alkyl, lower alkanoyl or lower alkoxycarbonyl, a 1-oxide of such compound of the formula IA, and salts thereof.

11. A compound according to claim 7 of the formula IB, wherein X is tert.-butyloxycarbonylamino, 2,2,2-trichloroethoxycarbonylamino, 4-methoxybenzyloxycarbonylamino, diphenylmethoxycarbonylamino or tritylamino, R₂ is 2,2,2-trichloroethoxy, 2-iodoethoxy, 2-chloroethoxy or 2-bromoethoxy, phenacyloxy, benzyloxy, methoxybenzyloxy, nitrobenzyloxy, diphenylmethoxy, 4,4'-dimethoxydiphenylmethoxy, or trimethylsilyloxy, and R₃ is lower alkyl, and salts thereof.

12. A compound according to claim 7, which is the 7β-[D-α-tert.-butyloxycarbonylamino-α-(1,4-cyclohexadienyl)-acetylamino]-3-methoxy-3-cephem-4-carboxylic acid diphenylmethyl ester.

13. A compound according to claim 7, which is 7β-[D-α-tert.-butyloxycarbonylamino-α-(1,4-cyclohexadienyl)-acetylamino]-3-methoxy-2-cephem-4-carboxylic acid diphenylmethyl ester.

14. A compound according to claim 7, which is the 7β-[D-α-(1-methoxycroton-3-ylamino)-α-(1,4-cyclohexadienyl)acetylamino]-3-methoxy-3-cephem-4-carboxylic acid or a salt thereof.

15. The antimicrobial pharmaceutical composition which comprises a therapeutically effective amount of a pharmacologically active compound of claim 1, together with a pharmaceutically usable excipient.

16. The antimicrobial pharmaceutical composition which comprises a therapeutically effective amount of the pharmacologically active compound of claim 5, together with a pharmaceutically usable excipient.

17. The method of treating infections caused by microorganisms which comprises administering the pharmaceutical composition of claim 15.

18. The method of treating infections caused by microorganisms which comprises administering the pharmaceutical composition of claim 16.

* * * * *